(12) United States Patent
Kangastupa

(10) Patent No.: US 11,071,643 B2
(45) Date of Patent: Jul. 27, 2021

(54) OCULAR THERAPEUTICS TOOL

(71) Applicant: Visionisti Oy, Seinäjoki (FI)

(72) Inventor: Timo Kangastupa, Seinäjoki (FI)

(73) Assignee: Visionisti Oy, Seinäjoki (FI)

(*) Notice: Subject to any disclaimer, the term of this patent is extended or adjusted under 35 U.S.C. 154(b) by 877 days.

(21) Appl. No.: 15/528,613

(22) PCT Filed: Nov. 24, 2015

(86) PCT No.: PCT/FI2015/050817
§ 371 (c)(1),
(2) Date: May 22, 2017

(87) PCT Pub. No.: WO2016/083669
PCT Pub. Date: Jun. 2, 2016

(65) Prior Publication Data
US 2017/0266045 A1    Sep. 21, 2017

(30) Foreign Application Priority Data

Nov. 28, 2014  (FI) ..................................... 20146046

(51) Int. Cl.
*A61F 9/00* (2006.01)
*A61M 5/46* (2006.01)
*A61F 9/007* (2006.01)

(52) U.S. Cl.
CPC .......... *A61F 9/0026* (2013.01); *A61F 9/0008* (2013.01); *A61M 5/46* (2013.01); *A61F 9/007* (2013.01); *A61F 2250/0007* (2013.01)

(58) Field of Classification Search
CPC ...... A61F 9/0026; A61F 9/0008; A61F 9/007; A61F 2250/0007; A61M 5/46
See application file for complete search history.

(56) References Cited

U.S. PATENT DOCUMENTS 2,874,694 A    2/1959  Blackman
4,373,526 A    2/1983  Kling
(Continued)

FOREIGN PATENT DOCUMENTS

EP    2510902 A1    10/2012
EP    2589401 A1     5/2013
(Continued)

OTHER PUBLICATIONS

Notification of Reason of Refusal received for Japanese Patent Application No. JP2017-547077, dated Aug. 20, 2019, 16 pages including 9 pages of English translation.
(Continued)

*Primary Examiner* — Nathan R Price
*Assistant Examiner* — John A Doubrava
(74) *Attorney, Agent, or Firm* — Ziegler IP Law Group, LLC

(57) ABSTRACT

An ocular therapeutics tool including a stabilizer including a hollow body and a base connected to the body, the hollow body extending from the base, and the base being adapted to fit the eye surface, and an injection guide connectable to the stabilizer and adapted to receive an injection needle, wherein the injection guide includes at least one stopper adapted to define the injection depth of a needle inserted into the injection guide. The present application also provides an injection guide. The present application also provides a kit with the tool or the injection guide.

31 Claims, 15 Drawing Sheets

(56) References Cited

U.S. PATENT DOCUMENTS

| | | | |
|---|---|---|---|
| 5,141,496 A | | 8/1992 | Dalto et al. |
| 5,540,657 A | * | 7/1996 | Kurjan ................ A61F 2/0059 |
| | | | 137/614.11 |
| 6,241,709 B1 | | 6/2001 | Bechtold et al. |
| 7,824,372 B1 | | 11/2010 | Kurup |
| 2001/0044606 A1 | * | 11/2001 | Inkpen ................ A61M 5/3287 |
| | | | 604/181 |
| 2002/0165500 A1 | | 11/2002 | Bechtold et al. |
| 2003/0060763 A1 | | 3/2003 | Penfold et al. |
| 2010/0152646 A1 | | 6/2010 | Girijavallabhan et al. |
| 2010/0292642 A1 | * | 11/2010 | Kurup ................ A61F 9/0017 |
| | | | 604/116 |
| 2010/0318034 A1 | * | 12/2010 | Goncalves ........... A61F 9/0017 |
| | | | 604/174 |
| 2012/0271272 A1 | | 10/2012 | Hammack |
| 2013/0253416 A1 | * | 9/2013 | Rotenstreich ......... A61F 9/0017 |
| | | | 604/22 |
| 2014/0052140 A1 | * | 2/2014 | Sayegh .............. A61B 17/0231 |
| | | | 606/107 |
| 2014/0088552 A1 | * | 3/2014 | Soni ................ A61F 9/0026 |
| | | | 604/506 |
| 2014/0114243 A1 | * | 4/2014 | Smith ................ A61F 9/0026 |
| | | | 604/116 |
| 2015/0038905 A1 | * | 2/2015 | Andino ................ A61M 5/347 |
| | | | 604/117 |

FOREIGN PATENT DOCUMENTS

| | | |
|---|---|---|
| JP | H10504474 A | 5/1998 |
| JP | 2013543418 A | 12/2013 |
| RU | 2480186 C1 | 4/2013 |
| WO | 9501198 A1 | 1/1995 |
| WO | 9532749 A2 | 12/1995 |
| WO | 2007052730 A1 | 5/2007 |
| WO | 2008097072 A1 | 8/2008 |
| WO | 2010077136 A1 | 7/2010 |
| WO | 20120029082 A1 | 3/2012 |
| WO | 2012051575 A2 | 4/2012 |
| WO | 2012073180 A1 | 6/2012 |
| WO | 2013/121307 A1 | 8/2013 |
| WO | 2014043124 A1 | 3/2014 |
| WO | 2013104414 A1 | 7/2014 |
| WO | 20140179698 A1 | 11/2014 |

OTHER PUBLICATIONS

Partial Supplementary European Search Report; European Patent Office; EP Application No. 15864068.0; dated Jul. 2, 2018; 12 Pages.
International Search Report, Application No. PCT/FI2015/050817, dated Apr. 22, 2016, 6 pages.
Written Opinion of the International Preliminary Examining Authority, Application No. PCT/FI2015/050817, dated Oct. 3, 2016, 9 pages.
Written Opinion of the International Searching Authority, Application No. PCT/FI2015/050817, dated Apr. 22, 2016.
Finnish Patent and Registration Office, Office Action, Application No. 20146046, dated Mar. 27, 2015, 8 pages.
International Preliminary Report on Patentability, Application No. PCT/FI2015/050817, dated Jun. 22, 2016, 29 pages.
Olsen et al. "Suprachoroidal and Intrascleral Drug Delivery" U.B. Kompella and H.F. Edelhauser (eds.), Drug Product Development for the Back of the Eye, AAPS Advances in the Pharmaceutical Sciences Series 2, DOI 10.1007/978-1-4419-9920-7_8, Copyright American Association of Pharmaceutical Scientists, 2011, 12 pages.
Patel et al. "Suprachoroidal Drug Deliver to the Back of the Eyes Using Hollow Microneedles", National Institutes of Health, NIH Public Access, Author Manuscript. Published in final edited form as Pharm Res. Jan. 2011; 28(1): 166-176. doi: 10.1007/s11095-010-0271-y, 19 pages.
Patel et al. "Targeted Administration into the Suprachoroidal Space Using a Microneedle for Drug Delivery to the Posterior Segment of the Eye." Investigative Ophthalmology & Visual Science, Jul. 2012, vol. 53, No. 8, Copyright 2012 The Association for Research in Vision and Ophthalmology, Inc., 9 pages.
Extended European Search Report of European Patent Application No. EP15864068.0, dated Nov. 9, 2018, 14 pages.
European Patent Office, Notice of Opposition to a European patent, Application No. EP15864068.0, dated Oct. 14, 2020, 23 Pages.
Japan Patent Office, Decision to Grant a Patent, Application No. 2017-547077, dated Sep. 15, 2020, 3 Pages.

* cited by examiner

OCULAR THERAPEUTICS TOOL

FIELD OF THE APPLICATION

The present application relates to the field of ophthalmic therapies, and more particularly to local drug delivery to an eye and diagnostic sensing and stimulation of the eye.

BACKGROUND

It is often overlooked that the tissue site of action for many of ocular therapeutic agents is not the vitreous but the choroid and retina. As a result, a delivery method that can maintain therapeutic levels of a drug in the target tissues (i.e. choroid and retina) should provide more effective therapy for chorioretinal diseases, e.g. uveitis, age-related macular degenerations, diabetic retinopathy, diabetic oedema and glaucoma. This targeting can be accomplished by administering drugs into the suprachoroidal space (SCS). The SCS is a potential space located between sclera and choroid that can expand to accommodate a fluid or drug formulation (see for example Targeted Administration into the Suprachoroidal Space Using a Microneedle for Drug Delivery to the Posterior Segment of the Eye, Patel et al., Investigative Ophthalmology & Visual Science, July 2012, Vol. 53, No 8.).

Suprachoroidal drug delivery represents an improvement over current periocular and intravitreal (IVT) delivery methods, both of which are poorly targeted to the retinochoroidal sites.

In general, the intravitreal delivery of drugs is invasive, carries a risk of eye diseases, such as endophthalmitis, and often exposes and damages unintended tissues. Typically intravitreal injections and surgical placements of slow sustained-release drug delivery devices are subject to complications, such as haemorrhage, post-injection cataract formation, elevated IOP (intraocular pressure) and local drug toxicity. Intravitreal injections also usually require repeated injections. The implanted drug delivery devices that are used in connection with intravitreal administration are expensive and may need to be surgically removed or replaced.

Rather than injecting drugs outside the eye or in the vitreous humor, SCS enables precisely targeted injections, which bathes the retinochoroidal surface with the drug formulation. Moreover, by taking advantage of the unique features of ocular anatomy, SCS injections do not infuse the drug formulation in all directions from the injection site as in conventional injections. Instead, the drug formulation infuses circumferentially within the suprachoroidal space to cover a significant area of the back of the eye via a single injection. This method of delivery has several important attributes of an effective drug delivery system for the posterior segment (see for example Suprachoroidal Drug Delivery to the Back of the Eye Using Hollow Microneedles, Patel et al., Pharma Res. 2011 January; 28(01): 166-176. doi:10.1007/s11095-010-0271-y).

SCS injections result in higher drug levels in the target site, compared with IVT injection at the same dose. As a consequence, delivery to the SCS may enable more accurate dosing and reduction of the injection frequency. Also a slow and sustained drug release is possible by injecting for example biodegradable, encapsulated, nano- and microparticles and -materials or microbubbles. In addition, the targeted injections to the SCS decrease the exposure of non-targeted tissues to the drug. This is advantageous when delivering drugs, such as steroids, that can cause side effects, including cataracts and increased IOP (intraocular pressure) due to unintended drug diffusion to the lens and anterior segment of the eye (see for example Suprachoroidal Drug Delivery to the Back of the Eye Using Hollow Microneedles, Patel et al., Pharma Res. 2011 January; 28(01): 166-176. doi:10.1007/s11095-010-0271-y).

Compared to intravitreal injections, on SCS the drugs do not need to cross the internal limiting membrane of the retina in order to gain access to the outer retina, photoreceptors, RPE and choroid. Compared to the transscleral route, the suprachoroidal bypasses the diffusional barriers. Diffusional access to the choroidal stroma may have advantages, particularly if one is targeting a disease of the choroid. An example might include selective drug delivery in uveitis or in macular diseases that originate in the choroid or retinal pigment epithelium, respectively (see for example Suprachoroidal and intrascleral drug delivery, Olsen. T. & Gilger. B. in Drug Product Development for the Back of the Eye, 2011, U. Kompella & H. Edelhauser (Eds.)).

As opposed to intravitreal injections, injections to the suprachoroidal space do not cause direct vision problems, since drugs do not interfere with the optical pathway. The smaller wound is also likely to heal faster and be less painful for the patient. However, the injection depth must be controlled with high accuracy.

At present, on an investigational level, the SCS injections can be performed by using microneedles, which enable perpendicular insertion into the sclera, and reach the suprachoroidal space with a short penetration distance. In a clinical practice, in contrast, long conventional needles or cannulas are used by approaching the suprachoroidal space at a steep angle, i.e. with the needle nearly parallel to the ocular surface, taking a longer penetration path through the sclera and other tissue, increasing the size of the needle track and consequently increasing the risk of infection, choroidal bleeding, and/or vascular rupture. With such long needles, the ability to precisely control the insertion depth is diminished relative to the microneedle approach. Typically, the use of a hypodermic needle or cannula requires insertion nearly parallel to the ocular surface, which makes such injections challenging for the physician, therefore not providing a satisfactory approach. Such a method requires a surgical cut down of the sclera and involves physical contact with the choroid, both of which introduce risks of infection and choroidal bleeding, respectively (see for example Targeted Administration into the Suprachoroidal Space Using a Microneedle for Drug Delivery to the Posterior Segment of the Eye., Patel et al., Investigative Ophthalmology & Visual Science, July 2012, Vol. 53, No 8).

Thus, all currently known alternative methods for microneedle injections into the SCS are difficult and cumbersome, invasive, and too complex to be performed as a simple office procedure.

Therefore there is need for tools and methods for facilitating injections into the suprachoroidal space safely with high accuracy and reproducibility, preferably by using regular needles.

SUMMARY

One embodiment provides an ocular therapeutics tool, comprising a stabilizer comprising a hollow body and a base connected to the body, the hollow body extending from the base, for example perpendicularly, and the base being adapted to fit an eye surface, preferably to stabilize the eye and to keep the eyelids open, and an injection guide connectable to the stabilizer and adapted to receive a needle, wherein the injection guide comprises at least one stopper adapted to define the injection depth of the needle inserted into the injection guide. In one embodiment the needle is an injection needle. In one embodiment the injection depth is within the suprachoroidal space of the eye.

One embodiment provides an injection guide adapted to receive a needle, wherein the injection guide comprises at least one stopper adapted to define the injection depth of a needle inserted into the injection guide. In one embodiment the needle is an injection needle. In one embodiment the injection depth is within the suprachoroidal space of the eye.

One embodiment provides a stabilizer for an injection guide.

One embodiment provides a kit comprising said ocular therapeutics tool and optionally at least one needle and/or syringe and/or vial containing injectable substance, such as a medicament vial.

One embodiment provides a kit comprising said injection guide and optionally at least one needle and/or syringe and/or vial containing injectable substance, such as a medicament vial.

The main embodiments are characterized in the independent claims. Various embodiments are disclosed in the dependent claims. The embodiments recited in dependent claims and in the description are mutually freely combinable unless otherwise explicitly stated.

The embodiments provide an alternative tool and method for microneedle-based SCS injections. The embodiments make use of regular needles, such as hypodermic or solid needles, that are readily available and inexpensive, and easy to handle. Also a variety of other needles and devices may be used, such as optical fibers, controllably biodegradable needles, extension tubes, medical injection pumps etc.

The embodiments make it possible, for instance, to deliver substances into the cortex of the eye by using a regular injection needle in a reproducible and safe manner. The injections may be targeted to any tissue, space or potential space in the eye, such as into a layer or between two layers, for example into sclera and/or cornea. A potential space is a space that can occur between two adjacent structures that are normally pressed together.

The tool described in the embodiments is particularly advantageous in making injections to suprachoroidal space, which is located between the choroid and the sclera. The tool is also applicable to injecting into intrascleral space, deep lamellar scleral space, Bruch's membrane, the retinal pigment epithelium, the subretinal space, the ciliary body, the trabecular meshwork, the aqueous humor, the vitreous humor, subconjunctival space, sub-Tenon's spaces, Tenon's capsule, corneal stroma and other ocular tissues or neighboring tissue in need for the treatment. In one embodiment the injection depth is within cornea. Examples of suitable target layers in the cornea include corneal epithelium, Bowman's membrane, corneal stroma, Descemet's membrane, Dua's Layer and corneal endothelium. However, a cornea does not have a space or a potential space and therefore large volumes of substances cannot be usually injected into cornea. In one example a needle covered with an injectable substance may be used in such cases.

From the practitioners' point of view, the tool according to embodiments offers better globe stability, fixed repeatability of entry site positioning, depth and angle, ensuring a more predictable, standardized, faster and safer procedure. Therefore, it helps to reduce errors and compliance problems. Additionally, the tool simplifies the required surgical skills to perform a safe ocular injection for the less experienced. Because of its ease of use, more health care professionals could potentially use it, which would increase the efficiency of the process. SCS administration of the drugs will require only a non-surgical procedure during a routine visit. The tool may be used by a variety of users, such as doctors, nurses, physicians, ophthalmologists etc.

The injection guide covering the needle works also as a protective safety guard, ensuring that the medical staff doesn't accidentally hurt themselves. There is also no risk of needle contamination by the eyelashes for instance. The described tool is relatively inexpensive.

From the patients point of view, it has been suggested that placing a mould over the entire circumference of the limbus may act as physical anaesthetic block to the ciliary nerves. This leads to a blunt but firm pressure, which significantly reduces the discomfort and pain perception. The stabilization gives the patient a sturdy and comfortable feeling of the process. The stabilizer makes the needle and injection practically invisible to the patient.

The embodiments make it possible to effect a perpendicular injection to the SCS or other layer of the eye by using a regular, long injection needle such as a hypodermic needle. Until now, such injections have been done as a surgical procedure, with considerably steeper injection angles, nearly parallel to the ocular surface.

The embodiments also provide improvements in defining the injection depth and the exact injection point in a reliable manner when using a regular injection needle.

The feature that the stabilizer and the injection guide are separate parts and connectable, preferably removably connectable, provides several effects. The syringe and needle may be carefully inserted into the injection guide before carrying out the actual injection, so it is possible to ensure that the needle is actually fully inserted and contacts the stoppers inside the injection guide. This decreases the risks of incomplete needle insertion and injections which are not directed to the desired target.

The effective length of the needle may be adjusted accurately before the injection guide is brought to the injection site. A patient-specific injection depth may be obtained with high accuracy and repeatability.

In case of improper injection depth the injection guide with the needle and syringe may be removed from the stabilizer and a new injection depth may be obtained, for example by adjusting or by picking a new injection guide, while the stabilizer remains in the eye. Also a new injection with another needle and/or injection guide may be carried out while the stabilizer remains in the eye. For example another substance may be injected subsequently after a first injection.

If the injection guide is provided in a kit positioned in such way that it can be picked directly with a needle in a syringe, a risk of contaminating the needle, syringe and injection guide is decreased.

BRIEF DESCRIPTION OF THE DRAWINGS

In FIG. 4A, the guide is shown in a cross-sectional view. In FIG. 4B, the guide is shown from above, by looking through it.

In FIG. 5A, the guide is shown in a cross-sectional view. In FIG. 5B, the guide is shown from above. In FIG. 5C, the parts of the injection guide are shown separately. In FIG. 5D, the guide is shown as connected to a base of the tool via a support arm. In this embodiment, the injection point is about 10 mm from the limbus.

FIG. 11A shows a perspective view of a second part of the injection guide from side, FIG. 11B shows a perspective view of a first part of the injection guide from side, and FIG. 11C shows a view to the inside of the first part seen from the first end of the injection guide.

DETAILED DESCRIPTION

Figure 1:
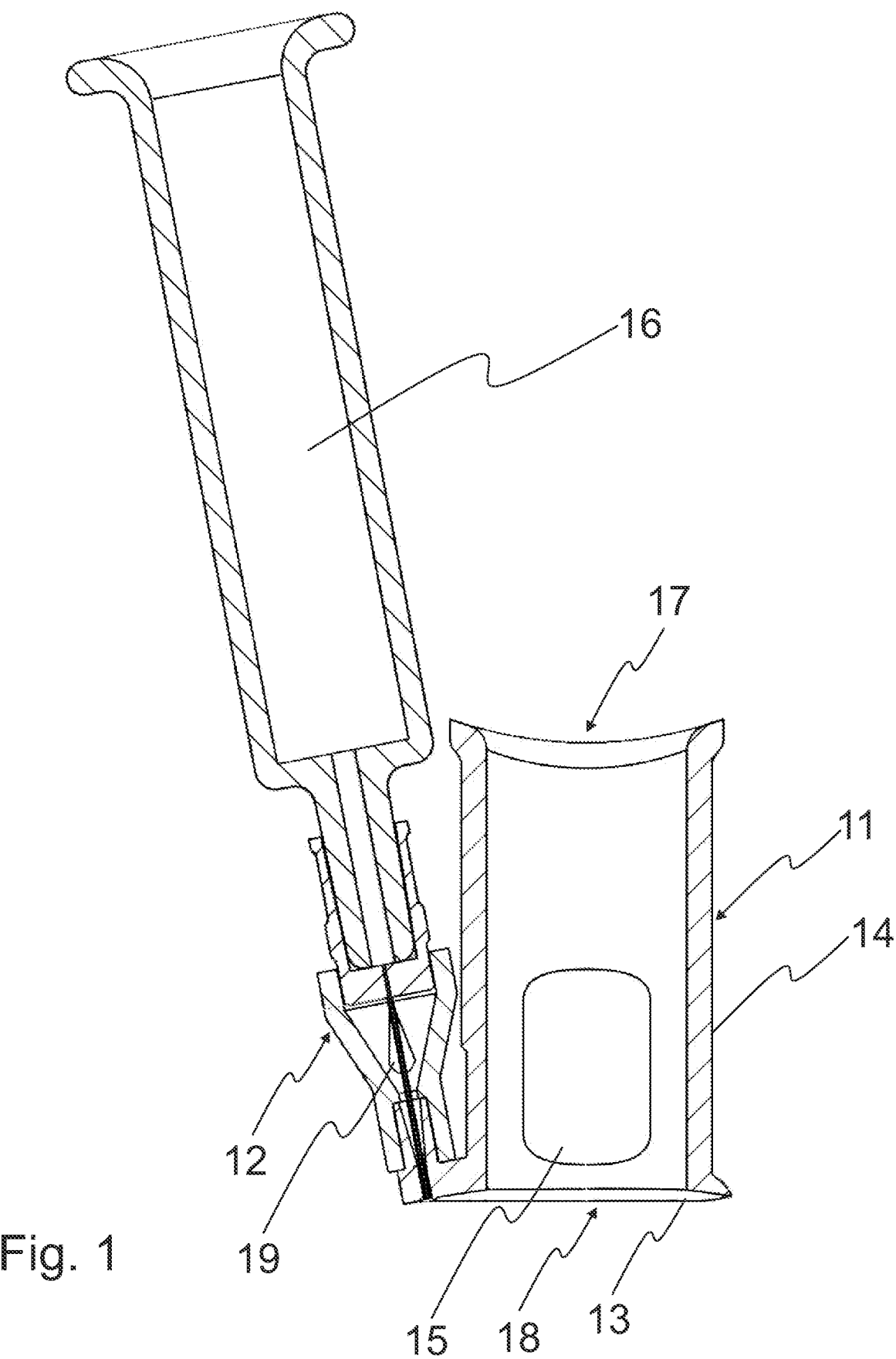
FIG. 1 shows an ocular therapeutics tool according to an embodiment in a cross-sectional view. In this embodiment, the injection point is about 3.5 mm from the limbus.
Figure 2A:
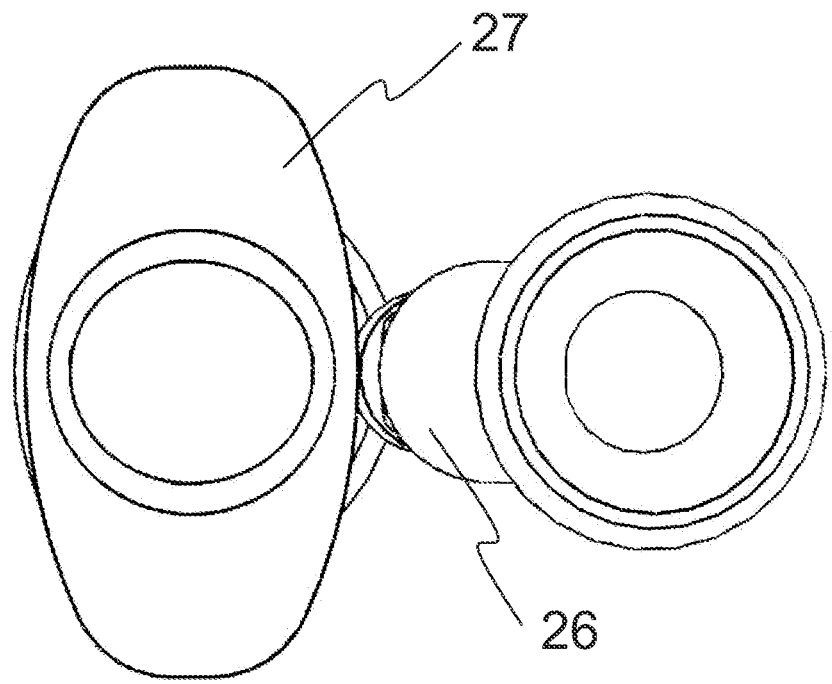
FIG. 2A shows the tool of FIG. 1 from above.
Figure 2B:
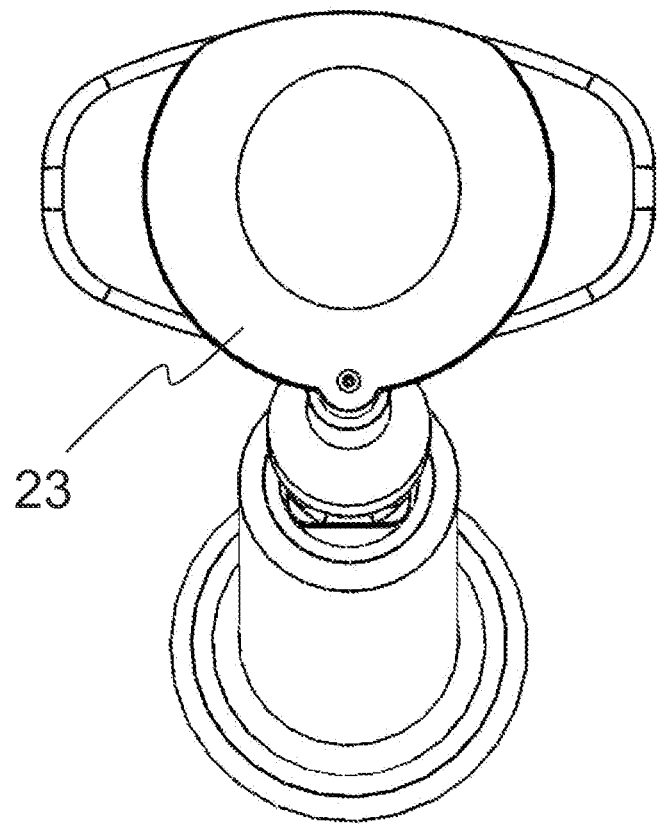
FIG. 2B shows the tool of FIG. 1 from below.
Figure 3:
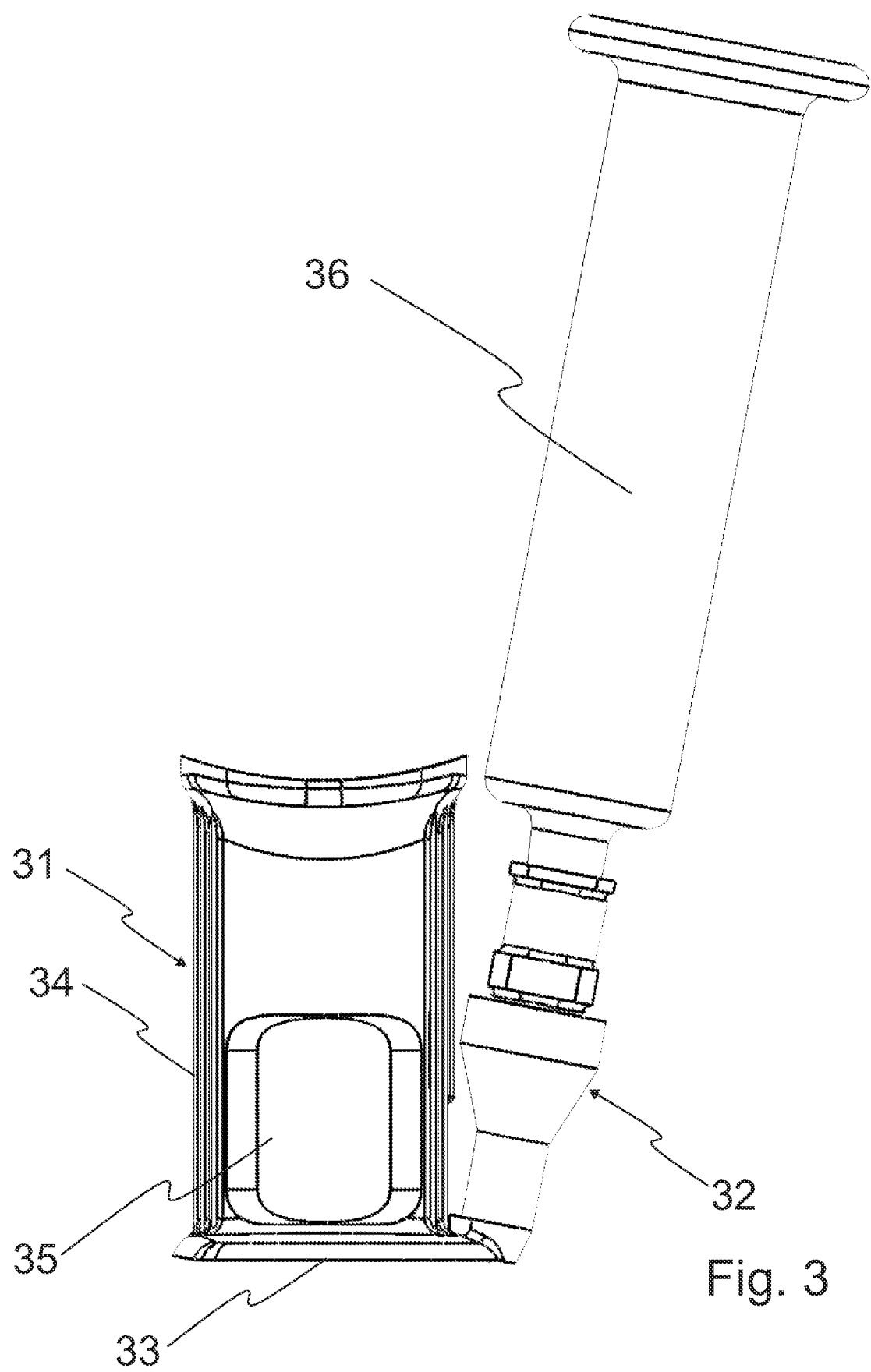
FIG. 3 shows the tool of FIG. 1 in a side view.

An ocular therapeutics tool according to embodiments is described in the following with reference to the drawings.

One embodiment provides an ocular therapeutics tool for assisting injection into an eye, the tool comprising a stabilizer comprising a hollow body and a base connected to the body, for example to a lower part of the body, the hollow body extending from the base, and an injection guide connectable to the stabilizer and adapted to receive a punctuation member, such as an injection needle. The ocular therapeutics tool may also be called as injection tool, injection assistance, injection helper, or injection aid. The hollow body may extend perpendicularly from the base, or substantially perpendicularly. "Hollow" as used herein means that the inside of the body is open, for example in such way that the iris of an eye can be seen through the body when inserting the stabilizer into an eye, which helps centering the tool. The base being connected to the body means that the base is integral part of the body, i.e. the body comprises the base.

The lower part of the body refers to the part of the body 11 which is close to the eye or in contact with the eye during use. The body has in general a first end 17 and a second end 18, wherein the second end 18 is the end which points to the eye during the use. In one example the body has a cylindrical shape, for example a tube-like shape. In one example the body has a frustoconical shape, i.e. having the shape of a frustum of a cone, wherein the second end has a smaller diameter than the first end. The body 11 is open at the first end 17 and at the second end 18 thus enabling the correct positioning of the tool in the eye. On the side of the body there may be one or more windows or openings, for example two windows on opposite sides. The window provides a view to the eye and may also enable surgical procedures on the eye. The length of the body, i.e. the length between the first end and the second end, may be in the range of 20-50 mm, for example 30-50 mm. In one example the length of the body is about 40 mm. Such a relatively high length of the body is especially suitable for a prominent canthus, i.e. to patients having the eyes deeper in their head, and the length provides more room for the user's fingers. Further, as the fingers are at a distance away from the injection site during the use also the safety is enhanced. The outer diameter of the body may be for example in the range of 10-30 mm.

The base 13 is located at the second end 18 of the body 11 of the stabilizer. The base 13 is adapted to fit the eye surface, for example to stabilize the eye and to keep the eyelids open. In one embodiment the base 13 comprises a flange 53, such as an annular support surface, adapted to fit the eye surface, as shown for example in FIG. 5D. The width of the flange may be in the range of 1-10 mm from the stabilizer, for example in the range of 3-7 mm, for example about 5 mm. In an example the base, or more particularly the flange, is concave to fit to the eye surface.

Figure 5A:
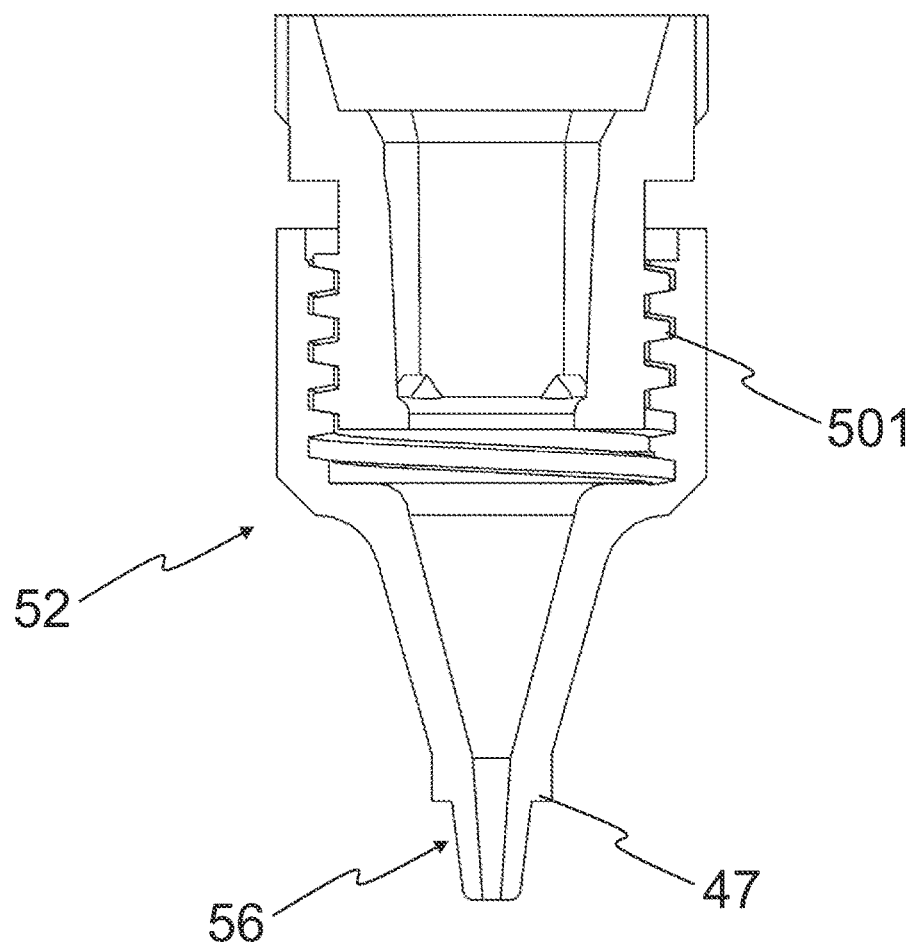
FIGS. 5A to 5D show an injection guide featuring adjustment means based on screw threads according to an embodiment.
Figure 5B:
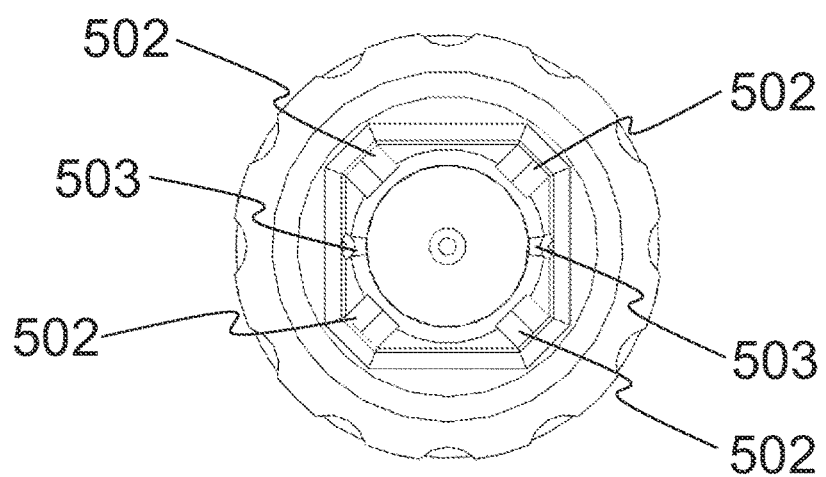
Figure 5C:
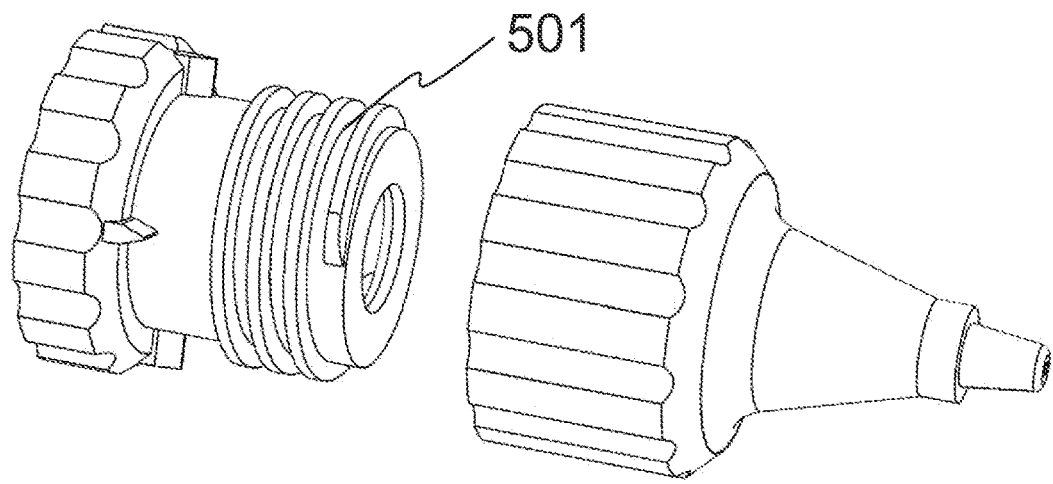
Figure 5D:
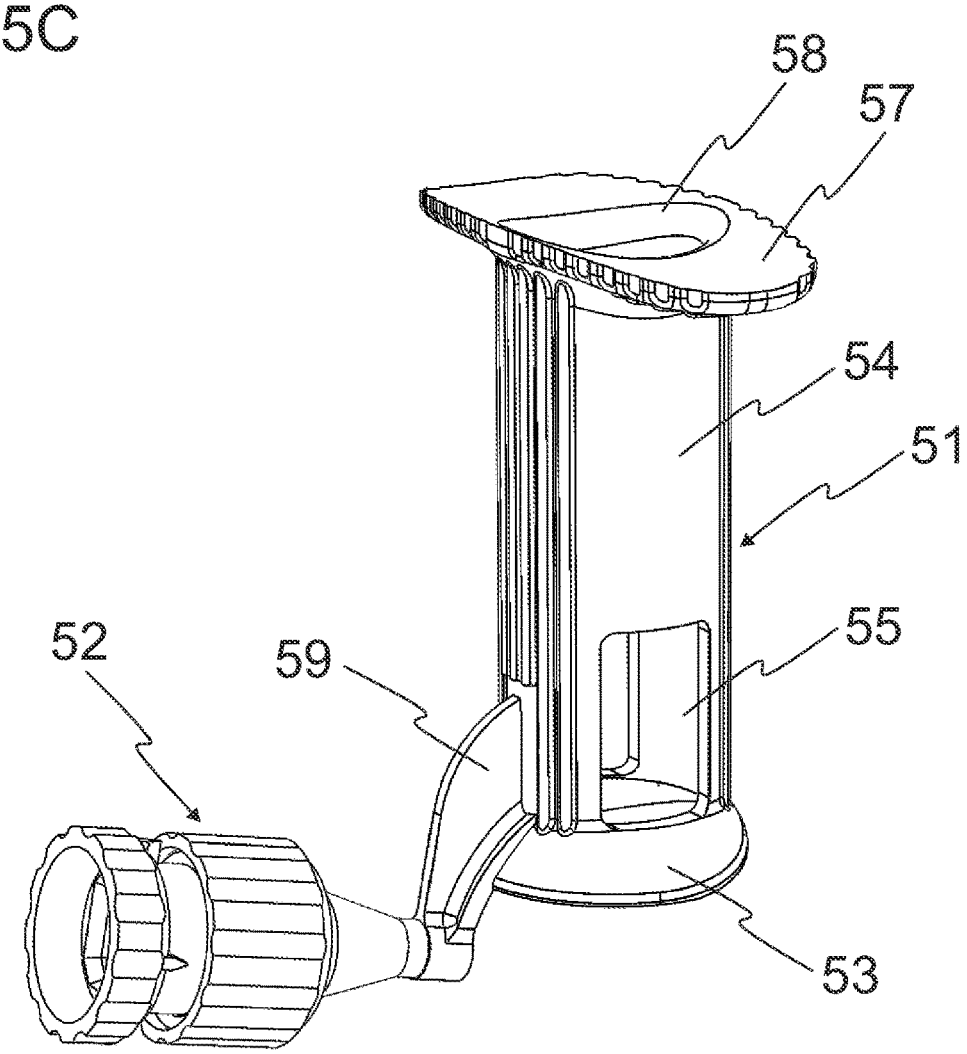

In one embodiment the injection guide is removably connectable to the stabilizer, which means that the injection guide, which is a separate part from the stabilizer, may be connected to the stabilizer and removed from the stabilizer, as can be seen in the figures. The stabilizer is adapted to receive the injection guide, i.e. the stabilizer and the injection guide are designed to physically fit to each other. The ocular tool is therefore two-parted i.e. it comprises two parts, the parts being the stabilizer 11, 31, 51, 71 and the injection guide 12, 32, 52, 72. In FIG. 5D the two parts are connected. The injection guide may be provided as removably connected to the stabilizer, and it is removably connected to the stabilizer during the use, more particularly during the injection.

In one embodiment the injection guide comprises a portion, such as a protruding part or a protruding portion 46, 56, adapted to fit to an aperture in the stabilizer adapted to receive the injection guide, preferably the injection guide is adapted to hold the needle approximately perpendicularly with regard to the eye surface, more particularly to the tangent plane of the eye surface, when the stabilizer is positioned onto the eye. The protruding portion may be for example a cylindrical portion 46 (FIG. 4A) or a frustoconical portion 56 (FIG. 5A, 5C) or any other suitable shape. The aperture in the stabilizer is adapted to receive the protruding portion 46, 56 in such way that the injection guide may be inserted and removed manually from the stabilizing part during the use. On the other hand the injection guide should fit into the aperture with such accuracy that the injection guide does not move substantially during the use. This may be implemented by using a suitable clearance between the aperture and the corresponding protruding part. In one example the clearance is in the range of 10-500 µm, such as 10-200 µm, for example 20-100 µm. In one example there is a shoulder 47 above the protruding portion of the injection guide, which shoulder will contact the edges of the aperture when the injection guide is inserted into the aperture. The shoulder may act as a stopper providing a hard stop for the injection guide thus limiting the reach of the protruding portion though the aperture. However, during the use the protruding portion will usually contact the eye surface before the stopper contacts the edges of the aperture. Therefore the stopper may act as a safety means preventing the user from inserting the injection guide too deep into the eye. In one example the movement of the injection guide through the base is not limited, for example there is no shoulder or the like acting as a stopper for the injection guide.

In one embodiment the aperture in the stabilizer is equipped with guiding means for guiding the insertion of the injection guide into the aperture. The guiding means may be for example a cone, such as a frustoconical part, providing a channel for the injection guide. The length of the guiding means, such as said cone, may be relatively short, for example 1-5 mm. In one example the guiding means does not limit the injection depth, i.e. the guiding means does not contain a stopper. In one example the guiding means contains a stopper for limiting the injection depth, i.e. said stopper contacts a corresponding stopper or other part in the injection guide, such as a shoulder and/or protruding part, as explained above. In one embodiment the aperture in the stabilizer does not comprise guiding means.

The location of the insertion site of the injection guide may have an effect to the delivery of the injectable substance into the eye and to the fluency of the treatment. The insertion site may be close to the body of the stabilizer. In such case the injection site is close to the limbus, and therefore the eyelids interfere with the injection less than if the injection site was more far away from the limbus. Also the moving of the tool irritates the eye surface less, especially if anaesthetic is used, which usually weakens the epithelia of the eye and may easily cause a loss of the epithelic tissue. Therefore the injection site may be in the base, for example in the flange. In one embodiment the flange comprises an aperture adapted to receive the injection guide.

The injection site may also be at a distance from the limbus, for example at a distance of 1-10 mm, such as 2-8 mm from the edge of the limbus. In one embodiment the injection guide is connectable to the stabilizer via a support arm 59 in the stabilizer. In one embodiment the support arm is adjustable or movable, which enables adjusting the injection site. In one example the length of the support arm may be adjusted. An adjustable support arm may contain adjusting and/or locking means for fixing a desired position of the injection site.

Figure 4A:
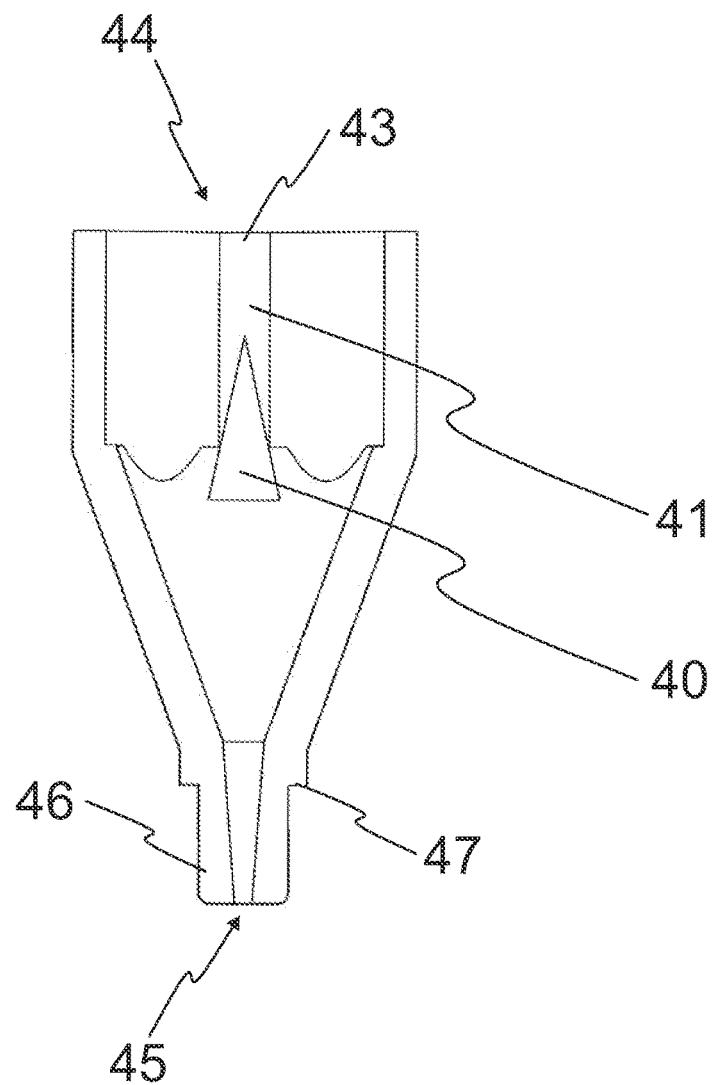
FIGS. 4A and 4B show an injection guide featuring fixed stoppers according to an embodiment.

The injection guide comprises a passageway adapted to receive a needle, or a hub or a connector of a needle, such as a channel, a bore, or the like through the injection guide. The injection guide has a first end 44 and a second end 45, wherein the needle enters the injection guide from an aperture 43 at the first 44 end and comes out from an aperture at the second end 45. The first end of the injection guide is adapted to receive the needle, or a hub or a connector of a needle, or a syringe. The protruding part or protruding portion 46, 56 of the injection guide is at the second end. 45, i.e. the protruding portion 46, 56 forms the second end 45 of the injection guide. The bore may be narrowed to the direction of the second end 45, for example in such way that the aperture at the second end is adapted to allow only the needle to pass, as can be seen in FIGS. 4A and 5A.

In one embodiment the stabilizer comprises a protruding portion adapted to receive the injection guide, as shown in FIG. 1. In this embodiment the injection guide comprises a channel or aperture for receiving the protruding portion in the stabilizer. In such case the needle must be inserted into an aperture in the protruding part.

Figure 15:
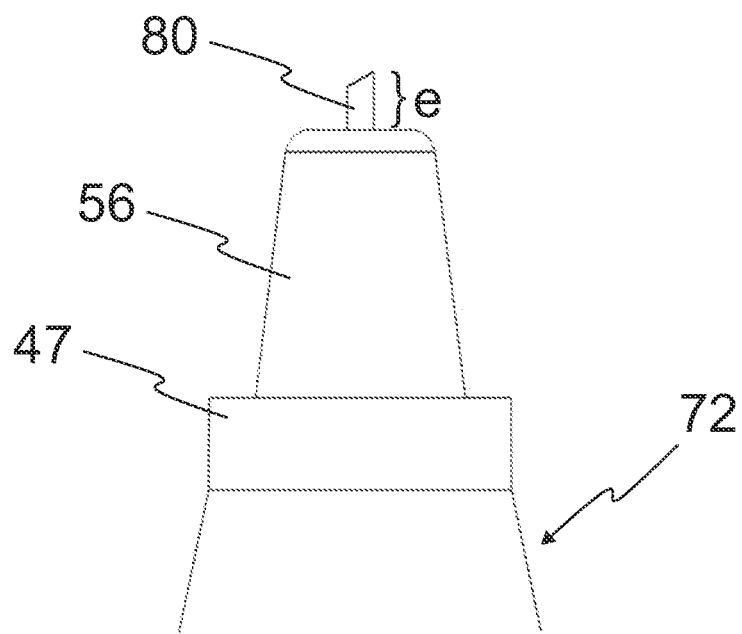
FIG. 15 shows a needle protruding from a second end of an injection guide and providing an effective length of the needle.

The injection guide comprises at least one stopper 40 adapted to define the injection depth of a needle inserted into the injection guide, for example within the suprachoroidal space of the eye. Alternatively, the injection guide comprises at least one stopper 40 adapted to provide an effective length of a needle inserted into the injection guide. The stopper may be selected from various alternatives described herein. In general the injection depth is less than 2000 µm, more particularly less than 1200 µm, or less than 1100 µm, even less than 1000 µm. The injection depth, i.e. the depth of penetration of the needle, is defined by the effective length (e) of the needle 80 protruding from the injection guide 72 (FIG. 15). The effective length (e) may be measured from the tip of the needle as in FIG. 15, or from the center of the lumen at the bevel of the needle. In one embodiment the injection depth is defined by providing an effective length of the needle protruding from the injection guide of less than 1200 µm. In one embodiment the protruding portion 46, 56 of the injection guide is adapted to contact the eye surface through an aperture in the stabilizer during the use. Therefore the protruding length of the needle corresponds with or is equal to the injection depth. When injecting to suprachoroidal space the injection depth, or correspondingly the effective length of the needle, may be for example in the range of 600-1200 µm. The expression "to define an injection depth within the suprachoroidal space of the eye" therefore comprises providing an effective length of the needle in the range of 600-1200 µm, or in another range or any other specific length or lengths disclosed herein. In one example the injection is targeted to cornea. An average thickness of a cornea is 545 µm, but may usually vary between 400 and 700 µm. When injecting to cornea the injection depth, or correspondingly the effective length of the needle, may be for example in the range of 50-700 µm, such as 100-700 µm, 200-700 µm, 300-700 µm or 400-700 µm. Said effective lengths refer to final effective lengths which are obtained after inserting the needle into the injection guide and optionally carrying out any adjustments to obtain the desired effective length of the needle.

Examples of ranges of effective lengths (e) suitable for injections into the suprachoroidal space include 500-1200 µm, 600-1200 µm, 700-1200 µm, 800-1200 µm, 500-1100 µm, 600-1100 µm, 700-1100 µm, 800-1100 µm, 500-1000 µm, 600-1000 µm, 700-1000 µm, 500-900 µm, 600-900 µm, and 700-900 µm. Specific examples of effective lengths include 400, 450, 500, 550, 600, 650, 700, 750, 800, 850, 900, 950, 100, 1050, 1100, 1150 and 1200 µm.

The injection guide comprises at least one stopper 40 adapted to define the effective length of the needle. The end 45 of the protruding portion 46, 56 of the injection guide may be flat or substantially flat, as can be seen for example in FIG. 4A, or it may be curved, for example convex or concave. A flat end of the protruding portion 46, 56 may have rounded edges as shown in FIG. 15. A flat or a substantially flat, i.e. non-curved (non-convex or non-concave) end of the protruding portion helps in defining the desired injection depth accurately and stabilizing the injection guide. The flat end enhances the contact with the eye surface and prevents leakage of the injectable fluid, especially if the end portion is made of flexible or elastic material. The diameter of the end 45 of the protruding portion 46, 56 may be in the range of 0.5-4 mm, for example 2-3 mm, or 1-2 mm. In one example, as used in the tests, the diameter of the end 45 of the protruding portion 46, 56 is about 1.5 mm.

In one embodiment the protruding portion comprises a flexible or an elastic part or portion, for example a part made of elastic material, for example having a disc-like shape and a thickness in the range of 0.2-1.0 mm. Such a flexible or an elastic portion may seal the connection between the injection guide and the eye surface at the injection site and prevents any leaking of injectable fluid. A flexible or elastic portion also provides a retract effect of the injection guide therefore enhancing the flow of the injectable substance. Also such a sealed junction helps keeping the injection site sterile and prevents any microbes from entering the wound. In one embodiment the aperture in the base comprises such a flexible portion, which will seal the injection site. In one example both the protruding portion and the aperture in the base comprise flexible parts or portions, which together seal the injection site.

In one example the tool comprises
a stabilizer comprising a hollow body and a base connected to a lower part of the body, the hollow body extending perpendicularly from the base, and the base being adapted to fit the eye surface, to stabilize the eye and to keep open the eyelids,
an injection guide connected to the stabilizer and adapted to receive an injection needle and to hold it approximately perpendicularly with regard to the eye surface, wherein the injection guide is further adapted to leave an injection point at the eye surface exposed and available for performing an injection through the injection guide,
wherein the injection guide comprises adjustment means for defining an injection depth within the suprachoroidal space of the eye. More particularly, the tool is adapted to leave an injection point at the eye surface exposed, and available for performing an injection through the injection guide.

In one embodiment the tool, or the stabilizer, is adapted to provide multiple injection points, leaving them at the eye surface exposed and available for performing an injection through the injection guide. The injection of the substance may be performed to each of the multiple injection points.

In one embodiment the tool comprises a protract-retract mechanism of a ratchet and plunger type. The protract-retract mechanism may be in the injection guide or in the connection between the injection guide and the stabilizer.

In the embodiments the adjustment means is
either one or more fixed stoppers with an upwards sloped shape, arranged on an inner surface of the injection guide, or a wire that penetrates the injection guide through its centre so that the needle is able to pass the wire from its either side, and/or mechanical screw threads.

One example provides a substance for use in the treatment of a trauma or an ocular disease, in which treatment the substance, such as a drug is delivered into the eye, such as into the suprachoroidal space of the eye, by using an ocular therapeutics tool described herein and a hypodermic needle, wherein an injection of the substance may be performed approximately perpendicularly with regard to the eye surface. The substance is usually provided as a solution, a dispersion, an emulsion or a suspension, such as aqueous solution or suspension, in general as an injectable fluid.

One example of such a substance is meso-zeaxanthin, which is a pigment at the back of the eye. Meso-zeaxanthin is an isomer of zeaxanthin. Meso-zeaxanthin is well suitable for injecting into the suprachoroidal space of the eye.

A wide variety of substances may be administered by using the tool described herein, including all known therapeutic substances which may be used for treating ocular diseases, disorders and traumas, and substances which act as a prophylactic or diagnostic agent. In one example the substance reduces, inhibits, prevents and/or ameliorates inflammation. The substance may be a drug or a prodrug.

Examples of suitable substances include antimicrobial agents including anti-bacterials, such as antibiotics (e.g. tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate); antifungals (e.g. chloramphenicol, chlortetracycline, ciprofloxacin, framycetin, fusidic acid, gentamicin, neomycin, norfloxacin, ofloxacin, polymyxin, propamidine, tetracycline, tobramycin, quinolones, amphotericin B and miconazole); anti-viral agents (e.g. idoxuridine trifluorothymidine, acyclovir, gancyclovir, interferon, cidofovir); anticancer chemo therapeutic agents; anti-inflammatory and/or anti-allergy compounds (e.g. steroidal compounds such as betamethasone, clobetasone, dexamethasone, dexamethasone 21-phosphate, fluocinolone, medrysone, fluoromethalone, betamethasone, triamcinolone, triamcinolone acetonide fluoromethalone, hydrocortisone, hydrocortisone acetate, prednisolone, methylprednisolone, prednisolone 21-phosphate, prednisolone acetate, and non-steroidal compounds such as antazoline, bromfenac, diclofenac, indomethacin, lodoxamide, saprofen, sodium cromoglycate); antibodies; antagonists (e.g. antagonist, a selectin antagonist, an adhesion molecule antagonist, platelet endothelial adhesion molecule (PCAM), vascular cell adhesion molecule (VCAM)), a leukocyte adhesion-inducing cytokine or growth factor antagonist (e.g. tumor necrosis factor-a (TNF-a), interleukin I β (IL-I β), monocyte chemotactic protein-1 (MCP-1), or a vascular endothelial growth factor (VEGF)), β-adrenoceptor antagonists (e.g. carteolol, cetamolol, betaxolol, levobunolol, metipranolol, timolol); miotics (e.g. pilocarpine, carbachol, physostigmine); sympathomimetics (e.g., adrenaline, dipivefrine); carbonic anhydrase inhibitors (e.g. acetazolamide, dorzolamide); chemotherapeutic agents, corticosteroids (e.g. Durezol), topoisomerase inhibitors (e.g. topotecan, irinotecan, camptothecin, lamellarin D, etoposide, teniposide, doxorubicin, mitoxantrone, amsacrine); prostaglandins, antiprostaglanding and prostaglandin analogs or prodrugs, e.g. bimatoprost and travoprost; aldose reductase inhibitors; artificial tear/dry eye therapies; local anesthetics (e.g. amethocaine, lignocaine, oxbuprocaine, proxymetacaine); cyclosporine, diclofenac, urogastrone and growth factors (e.g. epidermal growth factor, mydriatics and cycloplegics), mitomycin C, and collagenase inhibitors and treatments of age-related macular degeneration (e.g. pegaptanib sodium, ranibizumab, aflibercept and bevacizumab), thrombin inhibitors; antithrombogenic agents; thrombolytic agents; fibrinolytic agents; vasospasm inhibitors; calcium channel blockers; vasodilators; antihypertensive agents; inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); non-steroidal anti-inflammatories (e.g. salicylate, indomethacin, ibuprofen, diclofenac, flurbiprofen, piroxicam); antiallergenics (e.g. sodium chromoglycate, antazoline, methapyriline, chlorpheniramine, cetrizine, pyrilamine, prophenpyridamine); anti-proliferative agents (e.g. 1,3-cis retinoic acid); decongestants e.g. phenylephrine, naphazoline, tetrahydrazoline); miotics and anti-cholinesterase (e.g. pilocarpine, salicylate, carbachol acetylcholine chloride, physostigmine, serine, diisopropyl fluorophosphate, phospholine iodine, demecarium bromide); antineoplastics (e.g. carmustine, cisplatin, fluorouracil); immunological drugs (e.g. vaccines and immune stimulants); hormonal agents (e.g. estrogens, estradiol, progestational, progesterone, insulin, calcitonin, parathyroid hormone, peptide and vasopressin hypothalamus releasing factor); immunosuppressive agents, growth hormone antagonists, growth factors (e.g. epidermal growth factor, fibroblast growth factor, platelet derived growth factor, transforming growth factor beta, somatotropin, fibronectin); inhibitors of angiogenesis (e.g. angiostatin, anecortave acetate, thrombospondin, anti-VEGF antibody); dopamine agonists; radiotherapeutic agents; hyaluronic acid; peptides; proteins; enzymes; extracellular matrix components; ACE inhibitors; free radical scavengers; chelators; antioxidants; anti-polymerases; photodynamic therapy agents; gene therapy agents, such as DNA or RNA molecules or vectors containing thereof; and other therapeutic agents such as prostaglandins, antiprostaglandins, prostaglandin precursors, proteins, peptides and the like, agents effective to degrade collagen or GAG fibers in the sclera, pain relieving agents and local anesthetics; and stem cells for use in stem cell therapies.

Gene therapy may be used for treating for example retinitis pigmentosa, Stargardt disease, choroideremia, x-linked retinoschisis, achromatopsia, red-green color vision deficiency, and neovascular age-related macular degeneration. The viral vectors most commonly used for gene therapy are adeno-associated viruses (AAV). AAVs are simple (single-stranded DNA), nonpathogenic, and small in size (25 nm). Recombinant AAVs consisting of different serotypes and capsid proteins can be manufactured and designed to target cells in specific retinal layers, where they are capable of long-term expression of genes and proteins. Gene therapy has potential utility in the treatment of multiple retinal degenerative syndromes. It has been studied extensively for example in Leber congenital amaurosis (LCA)

In one example two or more substances are administered, either together or separately. In one example a substance is administered as microparticles or nanoparticles, or attached to microparticles or nanoparticles. Examples of microparticles include microspheres, microcapsules, microparticles and microbeads, which may have a number average diameter in the range of 1-100 µm, such as 1-50 µm, for example 1-25 µm. Nanoparticles may have a number average diameter in the range of 1-1000 nm, such as 1-500 nm. Any pharmaceutically acceptable carriers, excipients and/or vehicles may be included, such as water, saline, polymers, polysaccharides, surfactants, and the like. In one example the substance comprises a gelling agent, for example an agent which is configured to gel in the suprachoroidal space. Such a gelling agent may be used for providing a sustained and/or controlled release of a therapeutically active agent. Also other controllably or sustainably releasing agents may be included. In one example a substance is administered as an implant, such as an intravitreal implant, for example implants sold as trade names Retisert, Ozurdex, and Iluvien for treating diabetic edema.

Examples of the ocular diseases and disorders include age-related macular degeneration, diabetes-related eye disorder, such as diabetic macular edema, choroidal degeneration, fibrosis, glaucoma, inflammation, swelling, neovascularization, vein occlusion, ischemic eye disorders, ocular hypertension, retinoblastoma, retinitis pigmentosa, cancer, such as leukemia, sympathetic ophthalmia, temporal arteritis, uveitis and other eye diseases, disorders or traumas, or diseases, disorders or traumas of choroid or cornea.

Age-related macular degeneration (AMD) is a medical condition that usually affects older adults and results in a loss of vision in the center of the visual field (the macula) because of damage to the retina. In the dry (nonexudative) form, cellular debris called drusen accumulates between the retina and the choroid, causing atrophy and scarring to the retina. In the wet (exudative) form, which is more severe, blood vessels grow up from the choroid behind the retina which can leak exudate and fluid and also cause hemorrhaging.

Age-related macular degeneration, especially wet AMD, may be treated by injections into suprachoroidal space using for example antiangiogenics or anti-VEGF agents, such as a monoclonal antibody against VEGF-A, for example bevacizumab, ranibizumab, pegaptanib, pegpleranib and aflibercep, or other agents such as vitamins, verteporfin, lutein, zeaxanthine and meso-zeaxanthine.

Glaucoma may be treated for example with prostaglandins, for example latanoprost, bimatoprost or travoprost, beta blocker, alpha-adrenergic agonists, carbonic anhydrase inhibitors or mitotic or cholinergic agents.

In one embodiment the hypodermic needle penetrates the sclera only partially, so that the injectable substance, such as a drug, is able to seep into the suprachoroidal space under the sclera and above the choroid. The structure of the sclera is porous which enables the injectable substance to enter the structure. This is also safer as it is not necessary to target the tip of the needle exactly between the sclera and the choroid. The same effect may also be exploited when the needle is retracted from the injection depth, for example when using a protract-retract mechanism described herein, to obtain a better flow of the substance.

Before describing the embodiments in detail, it is to be understood that they are not limited to particularly exemplified apparatus, systems, structures or methods. It is also to be understood that the terminology used herein is for the purpose of describing particular embodiments only and is not intended to be limiting.

Exemplary tools are shown in FIGS. 1, 2A, 2B, 3, 5D, 13A and 13B. The tool comprises a stabilizer 11, 31, 51, 71 and an injection guide 12, 32, 52, 72. The stabilizer 11, 31, 51, 71 is adapted to stabilize the eye and to keep the eyelids open. The stabilizer comprises a base 13, 23, 33, 53 with an eye-contacting surface, for example a so-called flange, and a hollow body 14, 34, 54 extending perpendicularly from the base 13, 33, 53.

In one example the general shape of the hollow body 14, 34, 54 is a cylinder. Alternatively, the shape may be conical, with an upper opening larger than a lower opening, which enables easier inspection of the eye by the user. An open-top design assists in the centering on to the cornea by direct visualization.

In one example the inner cross-section of the body is oval-shaped, resembling the approximate shape of the cornea. In one example the inner length of the body is about 12 mm and the inner width of the body is about 11 mm. The outer cross-section of the body may be circular or oval. The inner length corresponds to an average horizontal diameter of a cornea and the inner width corresponds to an average vertical diameter of a cornea. In general the inner diameter of the body may be in the range of 10-14 mm, such as 10-13 mm. In one example the inner diameter in one direction is about 12 mm and in a perpendicular diameter about 11 mm.

The flange 13, 23, 33, 53 may be partly or completely flexible, for example made of elastic material, in order to facilitate its painless placement under the eyelids even for patients with narrow rima palpebrarum. The flange may also be non-flexible, and it may be made of the same material as the rest of the tool. In one example, when gently pushed on the eye, a controllably flexible flange will also urge the conjunctiva to slide over the underlying sclera. Thus, after withdrawal of the tool, the point of entry closes and seals quickly and completely. Sealing of the wound prevents substance reflux and decreases the risk of infections and other complications. The flange also prevents the eye lashes and the eyelid margins from coming into contact with the open wound. The edges of the flange must be rounded, i.e. they shall not be sharp or contain sharp edges, to prevent damaging the cornea when the stabilizer is applied into an eye and below the eyelids, and moved therein. However, the flange should be substantially thin and there should not be any junctures at the parts or portions which are in contact with the eye, especially the eye surface, during the use. In practice this means that if the flange contains an elastic portion, only the elastic portion is in contact with the eye during the use.

When the flange or other type of base contacts the eye surface, it may be tightly attached onto the eye under the eyelids. In such case tear fluid or other liquid, such as eye drop liquid, may be concentrated and/or rise into an injection channel in the stabilizer by capillary action. The injection channel refers to a channel in an ocular therapeutics tool whereto the needle is inserted. The rise of the fluid or liquid provides a risk of infection when the injection is carried out through the concentrated fluid or liquid. In the present device this effect is decreased as the injection guide is separate from the stabilizer and the injection channel through the base is relatively short. Further, the injection guide is connected to the stabilizer for a relatively short time. The effect does not reach the injection guide, and the capillary pressure is weak or it may be practically non-existent in the base. However, it is possible to effect to the capillary pressure by providing further apertures in the base near the aperture adapted to receive the injection guide, at the eye side of the base, for example one or more, or a plurality of apertures around the aperture adapted to receive the injection guide. These apertures may extend through the base, or they may be partial, i.e. cavities or pits, having a depth for example in the range of 0.2-1.0 mm. These further apertures may be for example round apertures smaller than the injection aperture, for example having a diameter of 1.0 mm or less, for example 0.2-1.0 mm, or they may be elongated apertures, for example extending radially from the aperture of the injection guide, and which may have a width of 1.0 mm or less, for example 0.2-1.0 mm, and a length of 5.0 mm or less, for example 0.5-5.0 mm. Also other shapes at the eye side of the base not extending through the base may be used, such as protruding portions or grooves, slots or ducts, which decrease the capillary pressure and may also facilitate the contact with the cornea. In one example the protruding portions are round portions, such as nodules, having a diameter of 1.0 mm or less, for example 0.2-1.0 mm. In one example the protruding portions are elongated portions, for example extending radially from the aperture of the injection guide, and which may have a width of 1.0 mm or less, for example 0.2-1.0 mm, and a length of 5.0 mm or less, for example 0.5-5.0 mm. The height of the protruding portions may be for example in the range of 0.2-1.0 mm. Such protruding portions may provide a slight movement of the cornea when the stabilizer is rotated.

In an embodiment, the base is connected to a suction ring (not shown) that acts in the same way as a suction cup. The suction rings are adapted to stabilize the eye further and they contain holes through which air can be sucked by means of a separate device, for example by means of a pump.

In an embodiment, the base is connected to an injection guide 12, 32, 52, 72 that is adapted to receive a device or a punctuation member, such as a conventional needle and syringe 16, 26, 36. In FIG. 1, the injection guide 12 is directly attached to the stabilizer 11, whereby the injection point is close to limbus. Alternatively, as shown in FIG. 5D, the injection guide 52 is connected to the stabilizer 51 via a support arm 59, whereby the injection point is further away from limbus.

The injection guide and its attachment to the stabilizer is constructed so that a part of the eye surface, that is the desired injection point, is left exposed and available for performing an injection through the injection guide. An "injection point" corresponds to the location, for example an aperture, in the stabilizer adapted to receive the injection guide, or more particularly a needle inserted into said injection guide.

In an embodiment (not shown), the ocular tool is constructed so that it provides multiple injection points at different distances from the limbus, e.g. a first injection point at the limbus, a second injection point at a distance of 3.5 mm from the limbus, a third injection point at a distance of 12 mm from the limbus, and/or a fourth injection point to the cornea, or any combination of these. The ocular tool may also provide multiple injection points at the same distance, e.g. around the limbus. The posterior injection point is preferably between the limbus and the equator. The ocular tool may also provide injection points with different angles in relation to the eye surface, the angles being different in at least one of X, Y or Z directions (in the Cartesian plane).

Multiple injection points can be implemented for example by providing multiple attachment points for the injection guide along one or more support arms and/or at a flange, for example at different sides of the body. Each of the injection points leaves the eye surface exposed and available for performing an injection through the injection guide. Injections of a substance can be performed sequentially or nearly simultaneously to all or part of the multiple injection points. The therapeutic effect of the injected substance, such as a fluid drug formulation, may be improved when conducting multiple injections to different injection points.

In an embodiment where the injection is made to the cornea, the injection guide is connected to the stabilizer so that the needle penetrates through an opening inside the inner cross-section of the body.

In an embodiment the injection guide is disconnected or separate from the rest of the tool, and used as an independent unit. Therefore one embodiment provides an injection guide adapted to receive a needle, such as an injection needle, wherein the injection guide comprises at least one stopper adapted to define the injection depth of a needle inserted into the injection guide, for example within the suprachoroidal space of the eye. Such a separate injection guide may be identical to the injection guide described herein in context with the stabilizer.

Figure 10:
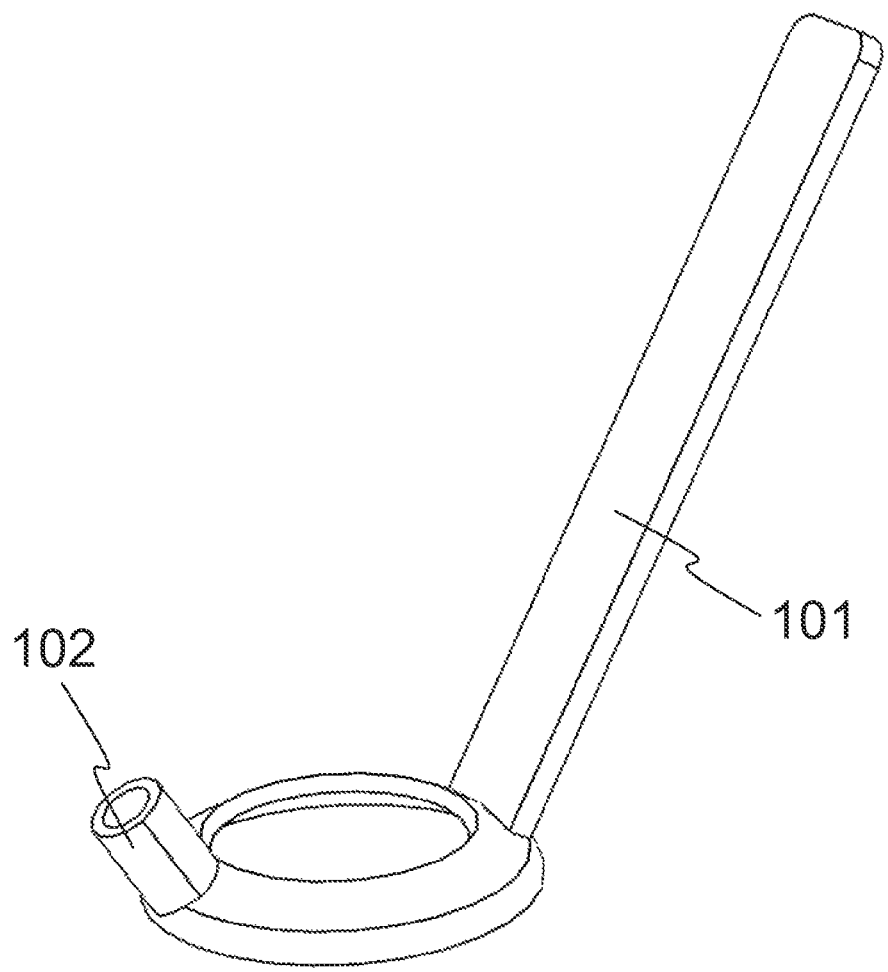
FIG. 10 shows an instrument that can be used in connection with an injection guide. This instrument does not include a speculum and is used without any stabilizer.

FIG. 10 shows an instrument that can be used in connection with an injection guide that does not include a speculum. The instrument comprises a handle or an arm 101 for facilitating, holding and positioning of the instrument, and a receiving means 102 for receiving and holding an injection guide. The instrument therefore acts as a stabilizer. The receiving means is adapted to receive the injection guide, i.e. the instrument and the injection guide are designed to physically fit to each other. The receiving means contains an aperture, which is adapted to receive the protruding portion 46, 56 of the injection guide in such way that the injection guide may be inserted and removed manually from the instrument during the use. On the other hand the injection guide should fit into the aperture with such accuracy that the injection guide does not move substantially during the use. In one embodiment the aperture in the instrument is equipped with guiding means for guiding the insertion of the injection guide into the aperture, as can be seen in FIG. 10. The guiding means may be for example cylindrical part or a cone, such as a frustoconical part, providing a channel for the injection guide. The length of the guiding means, such as said cone, may be relatively short, for example 1-5 mm. In general the receiving means may be similar to the corresponding part in the base of the stabilizer 71 as explained herein. The instrument of FIG. 10 may have an annular support surface adapted to fit the eye. In one example the support surface is a fully annular, i.e. circular. In one example the support surface is partly annular, i.e. it is C-shaped or it is open at one side, for example by 30-90 degrees, and does not form a full circle. Such an open part of an annular support helps seeing the border of the limbus when positioning the instrument into an eye.

Also other types of instruments or stabilizers may be used in connection with an injection guide. In one example such an instrument comprises a handle or arm for facilitating, holding and positioning of the instrument, and an angled portion at the end of the handle adapted to be placed into an eye. The angled portion acts as a base adapted to fit an eye surface and adapted to receive an injection guide. The angled portion contains an aperture for receiving the injection guide, which aperture may be in a flat portion adapted to contact the eye surface during the use. The angled portion may also contain an extended flange designed to keep lids and lashes away. The angled portion may be for example a portion formed from a stripe, such as a metal stripe. An example of such an instrument is Rapid Access Vitreal Injection guide (RAVI Guide) by Katalyst Surgical LLC.

In an embodiment, a stabilizer without an injection guide, with or without a arm or a handle, may be used as an independent unit. Therefore one embodiment provides a stabilizer for an injection guide, or for an ocular therapeutics tool, the stabilizer comprising a base adapted to fit an eye surface and adapted to receive an injection guide, such as the injection guide described herein. In one embodiment the stabilizer comprises a hollow body and a base connected to the body, the hollow body extending from the base, for example perpendicularly, and the base is adapted to fit an eye surface and adapted to receive an injection guide. The stabilizer may be identical to any stabilizer described herein. The injection guide may be the injection guide described herein. The base may contain an aperture for receiving an injection guide or a needle, with a guiding means or without it.

The injection guide is adapted to receive a needle, to hold it at a desired angle and to define an injection depth. The injection guide also protects the needle from contamination from e.g. eyelashes and protects the user, and thereby works as a safety needle.

The injection guide preferably has a tubular structure that extends from the base of the stabilizer, or from a support arm attached to the base, when inserted.

In an embodiment, the injection angle is approximately 90 degrees, for example 85 to 95 degrees to the tangent plane of an eye surface at the injection point. An angle close to 90 degrees provides a good control of both injection depth and injection point. In some cases, depending on the injection point, an injection angle different from 90 degrees may be preferable. In general, the injection in case of said 90 degrees is carried out at a normal to the surface of an eye at the injection point. By a definition in the three-dimensional case a surface normal, or simply normal, to a surface at a point P is a vector that is perpendicular to the tangent plane to that surface at P. In this case P is the injection point.

The injection angle may be also different, i.e. non-perpendicular to the tangent plane at the injection point, for example forming an angle in the range of 45-85 degrees to the tangent plane of an eye surface at the injection point, in general in at least one direction X-Y-Z. This may enable better access to peripheral tissue.

The thickness of the sclera or the cornea, and therefore also the injection depth, may vary between individuals. To obtain an injection depth to a desired location, especially to the suprachoroidal space of the eye, a specific effective length of the needle must be obtained. The thickness of the sclera of a patient may be measured and determined by using any suitable means, such as by using optical coherence tomography, UBM device or ultrasound device for example a B-scan. The thickness of the cornea of a patient may be measured and determined by using any suitable means, such as by using biometer, pachymeter, Scheimpflug camera, optical coherence tomography or UBM device or ultrasound device, for example an A-scan. The measurement is usually carried out separately before the operation, and the individual measurement results may be stored for later use. Therefore, briefly before the injection the effective length of the needle may be specifically adjusted for a patient according to the individual measurement results to obtain an accurate injection depth to the target tissue or location, such as to the suprachoroidal space of the eye. This may be called as patient-specific injection depth. The suitable injection depth may also be defined by trials, i.e. by monitoring when the medicament enters the desired location. If an injection is not successful, the length of the needle is adjusted, for example the length is increased, and a new injection to a slightly different location is carried out.

The injection guide may contain adjustment means for adjusting the injection depth. Such means may be manual, mechanic, electronic, fixed and/or adjustable. The adjustment may be stepwise or continuous.

Inside its tubular part, the injection guide may comprise one or more fixed stoppers that may function as an adjustment means, and are adapted to define the injection depth of a needle inserted into the injection guide.

Figure 4B:
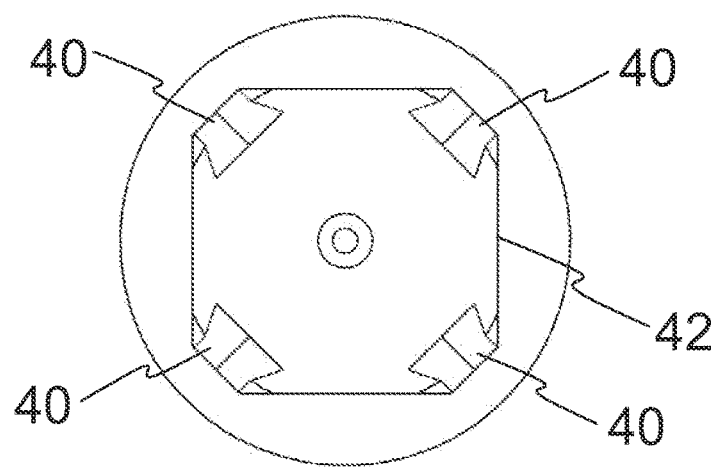

In an embodiment, the adjustment means or the stoppers comprise several mechanical, fixed stoppers 40 attached to and protruding from the inner surface 42 of the injection guide as shown in FIGS. 4A and 4B.

The injection guide may limit the injection depth only with regard to one direction by means of a protruding stopper 40. Alternatively, the stopper may extend from an inner edge of the injection guide to another inner edge. If there are several stoppers, they can cross each other. The stopper may impact its action for example to a hub, a syringe or another suitable part of a needle or other corresponding medical device.

In an embodiment, at least one stopper 40 is thin and comprises a sharp shape pointed towards the upper opening 43 of the injection guide so that the needle does not become damaged upon contact but gently slides towards the lower opening. It is possible to use multiple stoppers.

The at least one stopper 40 in the injection guide may be inside the injection guide, such as in a bore or a channel 41 or other passageway formed inside the injection guide adapted to receive a needle. In one embodiment the at least one stopper 40 is on the surface of the bore or channel 41. The amount of stoppers 40 may depend on the type of the stopper(s), on the type of needle, hub or the type of device in use, and it may be one, two, three, four, five or more. In one embodiment there are three stoppers 40. This stabilizes the construction as three points define a plane. In one embodiment the at least one stopper is adapted to contact the hub of the needle to stop the needle, or to limit the penetration of the needle into the injection guide. The part of the hub which is contacted by a stopper may be a shoulder in the juncture of the needle shaft and the hub, a glued portion in the juncture of the needle shaft and the hub, a protruding portion in a hub, or a flange at the syringe side of the hub. In one embodiment the injection guide comprises a bore for receiving the needle, and the edge surrounding the bore is adapted to act as a stopper. More particularly the stopper is at the first end of the injection guide, for example the edge of the first end surrounding the bore may act as a stopper adapted to receive the hub or the connector, for example a shoulder at the end of the hub or connector. The diameter of the bore may be adapted to receive the hub or the connector of a needle.

The needle as used herein refers to any suitable punctuation member, which terms may be used interchangeably, such as an injection needle. The punctuation member has a distal end portion, such as a tip of a needle, which is to be inserted into a target tissue. The punctuation member has, in general, a portion which may contact a stopper in the injection guide, such as an adaptor, a hub or a connector or a base gluing in the connection or juncture of the needle and the hub. A portion which contacts the stopper usually has a protruding portion, such as a shoulder, edge, protrusion, recessed edge, groove, nodule or the like which enables stopping the advance of the punctuation member into the injection guide.

In general a needle, such as an injection needle, has three parts: the hub, the shaft, and the bevel. The hub is at one end of the needle and is the part that attaches to the syringe. Sometimes it is also called as an adaptor, a connector or a connection. The shaft is the long slender stem of the needle that is beveled at one end to form a point. The bevel is the ground surface of a cannula or needle point, in practice the cutting edge of the needle. The hollow bore of the needle shaft is known as the lumen. The needle size is designated by length and gauge. The length of a needle may be measured from the juncture of the hub and the shaft to the tip of the point. The gauge of a needle is used to designate the outer radius of the needle. In one embodiment the injection needle is a hypodermic needle. Usually the shaft of a needle is made of stainless steel, but any other suitable materials may be used, such as other metals, plastics or biodegradable materials. In one type of needle the needle shaft is attached to a metal portion which is connected to the hub or a connector, or it forms a part of a hub or a connector. In one example such a metal portion has a square cross section.

The needle has usually also a connector, for attaching to the syringe barrel by means of a press-fit or twist-on fitting, such as Luer taper type of connector. The Luer taper is a standardized system of small-scale fluid fittings used for making leak-free connections between a male-taper fitting and its mating female part on medical and laboratory instruments, such as hypodermic syringe tips and needles or stopcocks and needles. There are two varieties of Luer taper connections: locking and slipping. The locking ("Luer-Lok") fittings are securely joined by means of a tabbed hub on the female fitting which screws into threads in a sleeve on the male fitting. The slipping, i.e. slip tip ("Luer-Slip") fittings simply conform to Luer taper dimensions and are pressed together and held by friction (they have no threads). In one embodiment the at least one stopper is adapted to contact the connector of the needle to stop the needle, or to limit the penetration of the needle into the injection guide.

A syringe as used herein refers to any suitable injector device, which terms may be used interchangeably, such as a medical injector, which is adapted to inject substance from a container through a punctuation member, such as a needle or the like. In one example the injector contains an actuator, such as a actuation rod, for example a piston or a plunger of a syringe, to which a force is exerted to produce movement of a distal end portion of the actuator within a substance container, which conveys a substance from the substance container into the target tissue via the punctuation member. One example of a substance container is a barrel of a syringe. The injector device may be manually operable, or it may be partly or completely automated, for example it may be connector to a pump or other machine-powered actuator device, and it may be controlled by a controller containing a processor configured to operate the actuator of the injector device.

The at least one stopper 40 may comprise an upwards sloped shape, arranged on an inner surface of the injection guide and directing the needle towards the center of the injection guide. Upwards as used herein refers to the direction of the first end of the injection guide 44 wherein the needle is inserted into or which is adapted to receive the needle. Sloped shape refers to a beveled shape which narrows and/or lowers towards the first end of the injection guide (FIG. 4A).

In one embodiment the injection guide comprises a bore 41 for receiving the needle, and the at least one stopper 40 comprises at least one projection, such as an elongated projection, on the surface of the bore parallel to the axis of the bore. The bore 41 may also be called a channel or passageway. The surface of the bore, i.e. the wall of the bore, is inside the injection guide, i.e. it is the inner surface of the injection guide. The projection refers to a protrusion extending from the surface of the bore 41 to the direction of the center of the bore 41. If the projection is an elongated projection parallel to the axis of the bore, it is also parallel to the direction of the insertion of the needle. An elongated projection has a length parallel to the axis of the bore, a height from the surface of the bore towards the axis of the bore, and a width perpendicular to the length and the height. An elongated projection has a first end pointing or corresponding to the first end of the injection guide and a second end pointing or corresponding to the second end of the injection guide. In general the width of an elongated projection may be in the range of 0.1-2.0 mm, such as 0.2-1.0 mm, measured at the second end of the projection. The height of the projection may be for example in the range of 0.5-3 mm, measured at the second end of the projection, such as 0.2-2 mm, or 0.5-1.2 mm, for example about 0.2 mm, about 0.5 mm, about 0.7 mm, about 1.0 mm, about 1.2 mm, about 1.5 mm, or about 2.0 mm. With an elongated projection the risk of the needle hitting or scratching the stopper is minimized. Further, in one embodiment the at least one projection, such as an elongated projection, is beveled in the longitudinal direction of the bore towards the first end of the injection guide, which end is adapted to receive the needle, as can be seen in the FIG. 4A or FIG. 11C. In one embodiment an elongated projection lowers towards the first end of the injection guide, i.e. the height of the projection decreases towards the first end of the injection guide. In one embodiment an elongated projection narrows towards the first end of the injection guide, i.e. the width of the projection decreases towards the first end of the injection guide. The narrowed end may be for example sharp or rounded. The width of the narrowed end may be for example in the range of 0.05-0.5 mm, such as in the range of 0.05-0.3 mm, for example in the range of 0.05-0.2 mm. In one example the projection both lowers and narrows towards the first end. Such beveled structures further lower the risk of the needle hitting or scratching the stopper. This provides an effect that the tip of the needle will not be damaged, and the needle does not scratch and remove any material from the injection guide. Also the needle can be inserted smoothly. However, the hub of the needle will be stopped by the stopper(s) 40 to define a desired effective length of the needle.

The stopper 40 may also have other shapes, which may also be called as projections or protrusions. In one embodiment the injection guide comprises a bore 41 for receiving the needle, and the at least one stopper 40 comprises at least one edge on the surface of the bore. The edge may form a shoulder, either fully or partly, around the bore. In one embodiment the at least one stopper is round or substantially round, such as a nodule. The height of the stopper, such as the edge, shoulder or nodule, may be for example in the range of 0.5-3 mm, such as 0.2-2 mm, or 0.5-1.2 mm, for example about 0.2 mm, about 0.5 mm, about 0.7 mm, about 1.0 mm, about 1.2 mm, about 1.5 mm, or about 2.0 mm. In one example there are more than one stoppers 40, such as can be seen in FIG. 4B wherein four stoppers 40 are shown. The cross-section of the bore or channel 41 may be circular or it may be angular, for example quadrangular as shown in FIG. 4B. The cross-section is adapted to be fitted to receive a device, such as a needle, a hub or a connector of the needle or other device. The stopper(s) may be located in the bore at a distance in the range of 1-20 mm from the first end of the injection guide, for example in the range of 2-10 mm.

In an embodiment (not shown), the at least one stopper is a thin limiting means, for example having a diameter in the range of 100-500 μm, such as a wire, that penetrates the injection guide through its centre, perpendicular to the main vertical axis of the guide, so that the needle is able to pass the wire from its either side.

In an embodiment, the faces of the stopper are sloped either upwards (see for example the stopper 19 in FIG. 1 and the stopper 40 in FIG. 4A) or downwards, directing the needle towards the center of the injection guide.

A sloped or wire-type shape in the stopper is advantageous because it prevents the needle from scratching against the stopper, which could lead to blunting of the needle. Such scratching could also lead to detaching of material from the surface of the injection guide, which material could end up in the eye. The user can be also certain that the needle actually becomes inserted into the eye and penetrates to the desired depth.

In one embodiment the injection guide comprises a bore for receiving the needle, and the at least one stopper comprises a wire crossing the bore of the injection guide, in one example perpendicular to the main vertical axis of the guide, so that the needle is able to pass the wire from its either side.

The stopper may be partly or completely controllably flexible. Controllably flexible refers to material which returns the needle when entered to obtain a better flow of the injectable solution. Such material may be elastic, for example elastomeric material, more particularly elastomer, such as rubber or the like. An elastomer is a polymer with viscoelasticity (having both viscosity and elasticity) and very weak inter-molecular forces, generally having low Young's modulus and high failure strain compared with other materials. The term, which is derived from elastic polymer, is often used interchangeably with the term rubber, although the latter is preferred when referring to vulcanisates. Each of the monomers which link to form the polymer is usually made of carbon, hydrogen, oxygen and/or silicon. Elastomers are amorphous polymers existing above their glass transition temperature, so that considerable segmental motion is possible. At ambient temperatures, rubbers are thus relatively soft and deformable. Examples of elastomers include unsaturated rubbers, such as natural polyisoprene, synthetic polyisoprene, polybutadiene, chlorophene rubber, butyl rubber, styrene-butadiene, or nitrile rubber. Other examples of elastomers include saturated rubbers, such as ethylene propylene rubber, epichlorohydrin rubber, polyacrylic rubber, silicone rubber, fluorosilicone, fluoroelastomers, polyethylene block amides, chlorosulfonated polyethylene or ethylene vinyl acetate. In one example the elastic material comprises synthetic rubber, for example neoprene. In one embodiment the elastomeric material is transparent or substantially transparent. In general "elastic material" as used in this application refer to the materials described above.

Preferably the stopper is located a certain distance inside the injection guide so that the needle must be pushed into the guide before it makes contact with the stopper. In this way the needle becomes automatically stable and directed to a proper position and angle.

In one embodiment the injection guide comprises adjustment means for adjusting the effective length of the needle. It may be necessary to adjust the effective length of the needle after the needle has been inserted into the injection guide. The effective length of the needle may be adjusted to obtain a patient-specific injection depth. This has been determined according to a patient's personal characteristics, such as previously measured thickness of the sclera or the cornea, wherein the distance from the surface of the eye to the desired location, such as to the suprachoroidal space, can be determined. The needle may penetrate through the sclera completely or partially. After the needle has been inserted into the injection guide, a preliminary effective length of the needle is provided. This may be zero or a value above zero, such as 50-700 μm, for example 50, 100, 150, 200, 250, 300, 350, 400, 450, 500, 550, 600, 650 or 700 μm. After this the length may be further adjusted to obtain a desired effective length of the needle, which may also be called as the final effective length of the needle. The effective length may be made longer, or shorter, according to the patient's personal characteristics. For example the length may be adjusted to obtain an effective length of the needle which is equal to the previously determined distance from the surface of the eye to the suprachoroidal space, also called as patient-specific injection depth.

The adjustment may be implemented by using different types of adjustment mechanisms. In one embodiment the adjustment means comprises screw threads. In such case the injection guide comprises two parts attached together with said screw threads, as shown in the FIGS. 5A-5D. Said two parts are adjustable in such way that the adjustment by screwing changes the effective length of a needle attached to the injection guide. The needle is attached to the first part 510, and the second part 512 is movable in relation to the first part. The first part comprises the at least one stopper adapted to define the injection depth of the needle inserted into the injection guide. As the needle protrudes from the second part, the effective length of the needle changes as the first and the second part move in relation to each other. In one embodiment the adjustment means is implemented with a screw having a wedge-shaped portion, wherein turning the screw moves the wedge portion between the first and the second part of the injection guide thus changing the distance of the first and the second parts.

In an embodiment shown in FIGS. 5A to 5D, the adjustment means are mechanical screw threads 501. In this embodiment, the injection guide further comprises fixed stoppers 502 and additional fixed stoppers for stabilization 503.

Figure 11A:
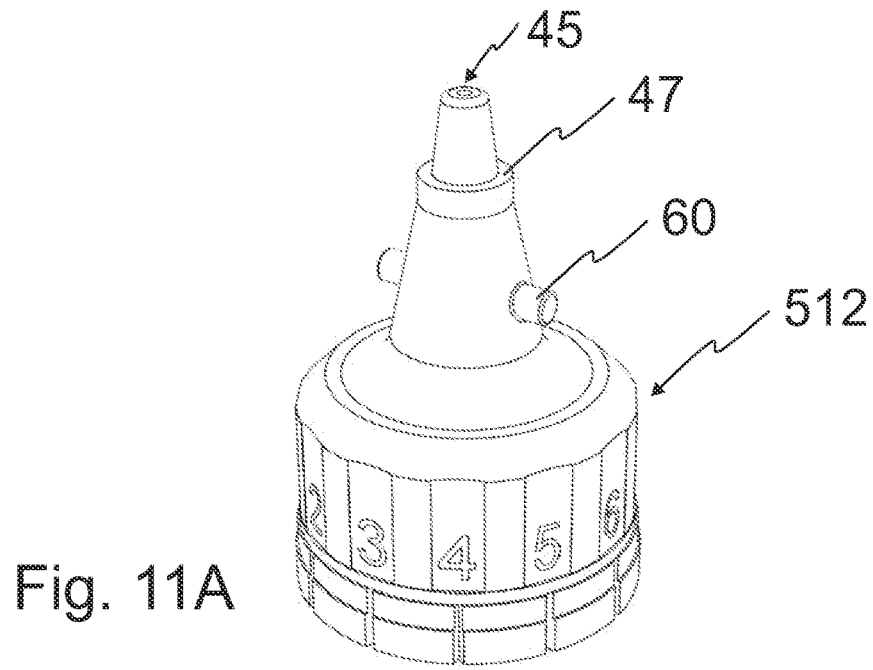
FIGS. 11A-C show embodiments of the injection guide.
Figure 11B:
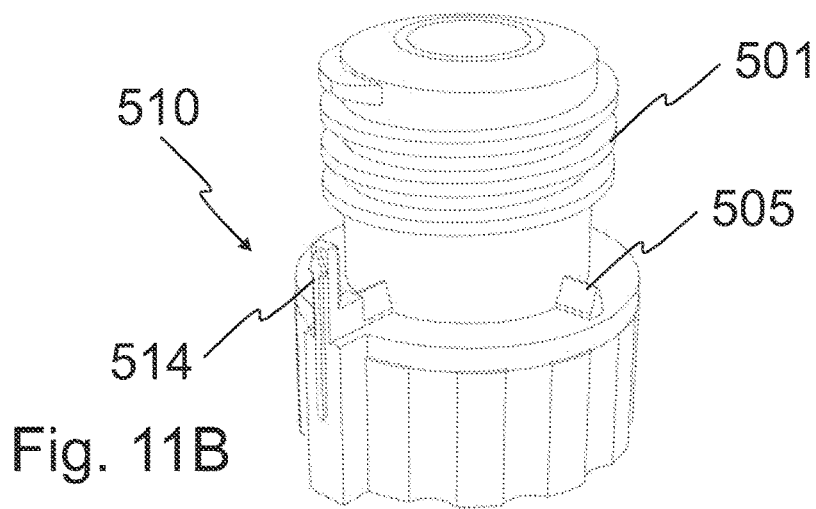
Figure 11C:
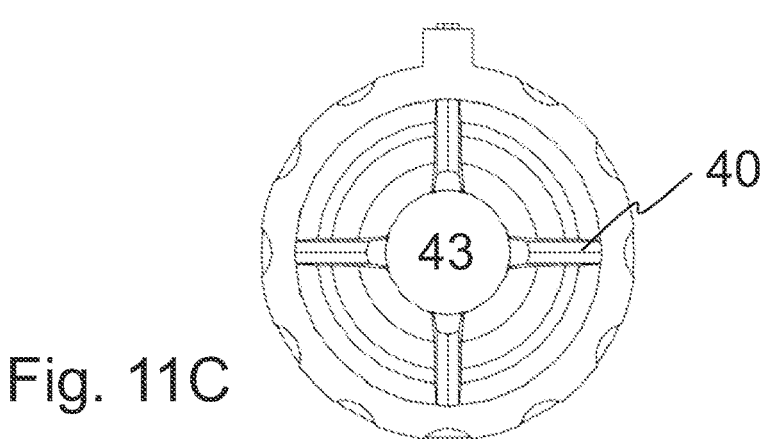

In one embodiment the means for adjusting the effective length of the needle comprises a stepwise adjustment. The stepwise adjustment may be implemented in such way that the adjustment of one step produces an audible and/or haptic indicator, such as a "clicking" sound. The steps may be arranged by predetermined intervals, such as intervals changing the effective lengths of the needle by for example 50 µm or 100 µm. Also an indicia or an indicator may be provided to indicate the adjusted effective length of the needle, such as lines, markings or the like indicating a measuring scale. FIGS. 11A and 11B show an example of an adjustment mechanism comprising screw threads with stepwise adjustment. The stepwise adjustment is implemented with wedge-shaped or beveled protruding portions 505 in the first part of the injection guide and in the second part of the injection guide, the protruding portions 505 being arranged to provide a hindrance in the adjustment when the edges of the protruding portions 505 in the first and in the second part meet. The hindrance can be overcome by applying more force, wherein a clicking sound will be obtained as an edge of the wedge-shaped portion pass a corresponding edge in the other part of the injection guide. One adjustment step is provided with each "click". The protruding portions and the screw threads are arranged to provide a predetermined adjustment with each step, i.e. "click", for example 50 or 100 µm in the effective length of the needle. The mechanism also contains a pointer 514 pointing to numerical values which represent different injection depths, each value representing one adjustment step. This can also be seen in FIGS. 13A and 13B.

The outer surface of the injection guide may comprise a visual indication that helps the user to push the needle up to the intended depth within the guide. In this way the user is able to ensure that the needle will penetrate the eye up to the desired injection depth. For example an indicia or an indicator may be provided to indicate the adjusted effective length of the needle, such as lines, markings or the like visual means indicating a measuring scale. In one embodiment the injection guide comprises an indicator means, more particularly a visual indicator means, for indicating the adjustable effective length of the needle, such as a measuring scale.

When the injection guide is connected to the stabilizer a connection is formed, for example a connection between the protruding portion of the injection guide and the aperture in the stabilizer. In one embodiment the connection between the protruding portion of the injection guide and the aperture in the stabilizer comprises locking means for stabilizing the needle when inserted.

In one embodiment the locking means comprise a bayonet type of coupling. Bayonet connector is a fastening mechanism comprising of a cylindrical male side with one or more radial pins, and a female receptor with matching L-shaped slot(s) and optionally with spring(s) to keep the two parts locked together. In one example the slots are shaped like a capital letter L with serif (a short upward segment at the end of the horizontal arm); the pin slides into the vertical arm of the L, rotates across the horizontal arm, then is pushed slightly upwards into the short vertical "serif" by the spring; the connector is no longer free to rotate unless pushed down against the spring until the pin is out of the "serif". In this case also the elasticity of the eye may push the injection guide upwards when it is not actively pushed against the eye.

In one embodiment the locking means comprise screw threads. It may be useful to allow the needle and/or the injection guide to be turned or rotated when inserting into the stabilizer or into the eye. Such rotating movement may be for example at least 30 degrees, such as about 90 or 180 degrees. In such case, the bevel of the needle will cut the tissue to prepare a channel for the medicament, i.e. a drilling effect is provided. In one embodiment the locking means comprise a pin 60 and slot combinations, wherein one part of the tool comprises at least one pin 60 and the other part comprises correspondingly at least one slot 62, wherein the pins 60 are arrange to fit to the slots 62 to lock the two parts together. In one example the stabilizer comprises a guiding means adapted to receive the injection guide, wherein the guiding means comprises said one or more slots 62, for example in a conical or frustoconical part, and a protruding portion or the second end of the injection guide comprises the corresponding pins 60. In one example there are two slots 62 and two corresponding pins 60 (FIG. 11A).

Figure 12A:
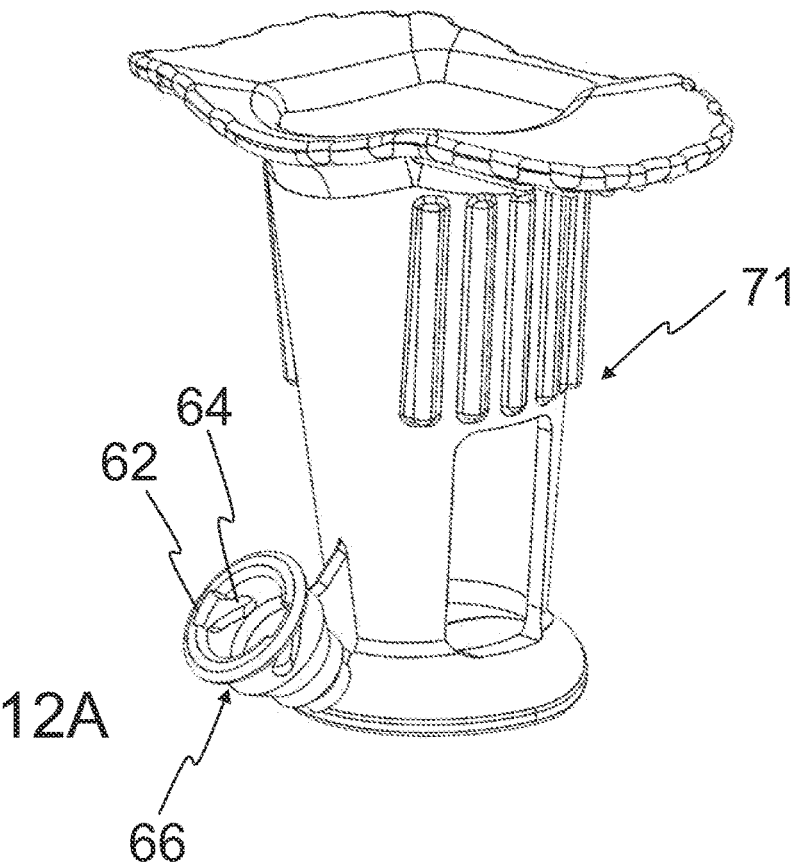
FIGS. 12A and 12B show views of an embodiment of a stabilizer.
Figure 12B:
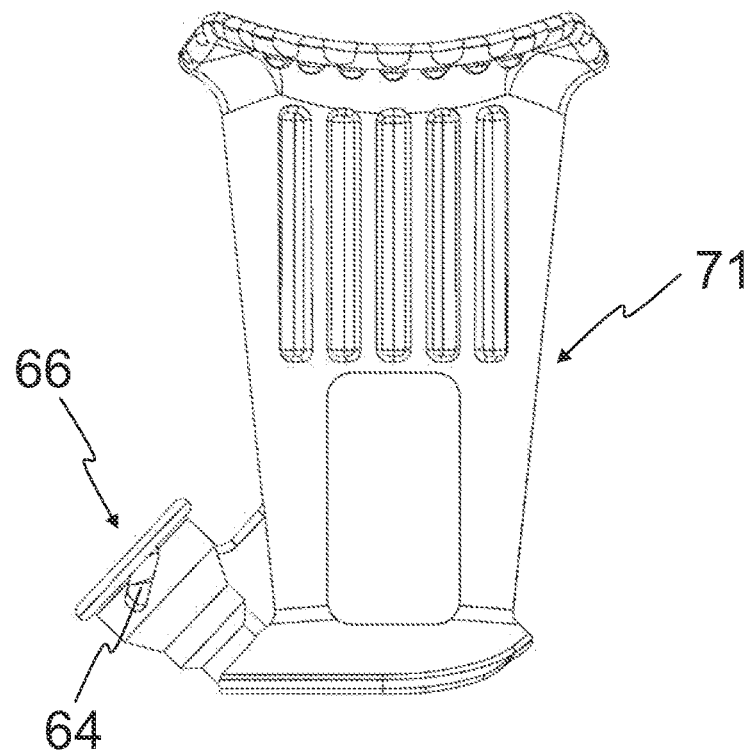

In one embodiment the guiding means is provided with a groove 64 adapted to receive a pin and to provide a rotating movement as shown in FIGS. 12A and 12B. The movement guided by the groove 64 may also force the injection guide towards the eye if the groove is provided as a spiral turn as shown in FIGS. 12A and 12B. Such as spiral turn may facilitate a rotating movement of at least 30 degrees, for example about 45, 90, or 180 degrees. In one embodiment the groove has a spiral part (or a screw thread part) and a non-spiral part which allows continuing rotating the injection guide without further proceeding into the eye. The non-spiral part continues from the spiral part, for example by 0.5-2 mm, into the direction of the circumference of the injection guide. In one embodiment the groove has a spiral part and a non-spiral part which allows the injection guide to retract from the farthest position, and also locks the injection guide into the stabilizer. In such case the non-spiral part continues from the spiral part back into the parallel direction to the axis of the injection guide, i.e. to the opposite direction to the injection direction, for example by 0.2-0.5 mm. This is similar to a locking often used in bayonet mount comprising the "serif".

Figure 13A:
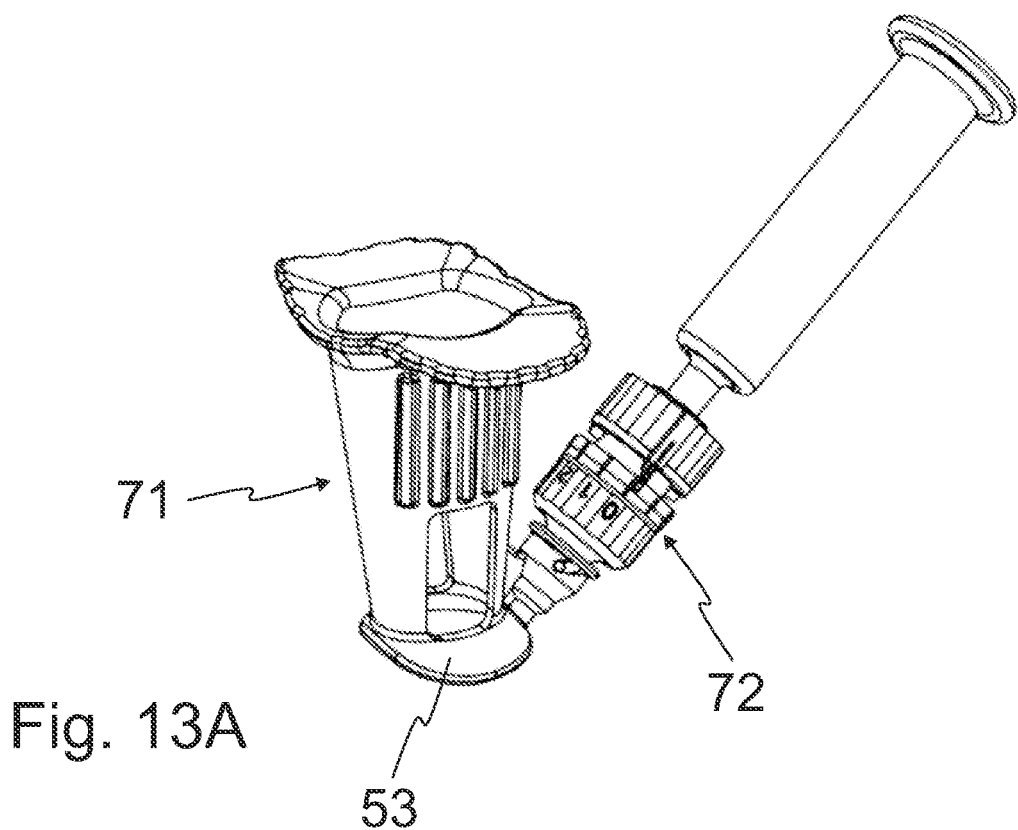
FIGS. 13A and 13B show perspective views of the ocular therapeutics tools wherein the injection guide and the stabilizer are connected.
Figure 13B:
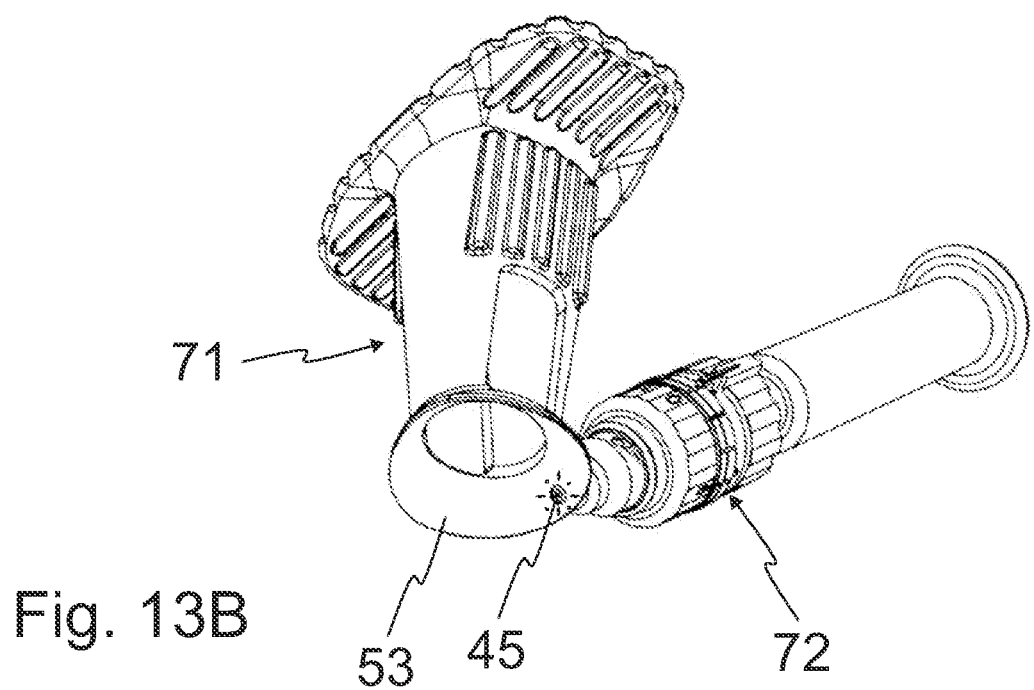

FIG. 11A shows a second part 512 of a two-parted injection tool having two pins 60 at the second end, said pins being adapted to fit to corresponding grooves 62 in the stabilizer 71. FIG. 12A shows a stabilizer 71 having a guiding means 66 for receiving an injection guide 12, wherein the guiding means have two grooves 62 for receiving two pins 60 in the injection guide. FIG. 13A shows an adjustable two-parted injection guide 72 with a syringe and a needle, wherein the injection guide 72 is inserted into said guiding means 66 in the stabilizer 71 in such way that the pins 60 are inserted into the corresponding grooves 62 in the substantially frustoconical guiding means, the grooves being arranged as a short spiral turn 64. FIG. 13B shows the same arrangement from the eye side wherein the second end 45 of the injection guide 72 with the needle protrudes through an aperture in a flange 53 in the stabilizer 71. As the flat side of the second end 45 of the injection guide 72 is arranged to protrude from the lower surface of the flange 53, i.e. the eye side of the flange 53, it is the flat side of the second end 45 of the injection guide which is in close contact with the eye surface, and therefore the length of the protruding part of the needle defines the injection depth, i.e. the effective length of the needle.

In one embodiment the connection between the protruding portion of the injection guide and the aperture in the stabilizer comprises a protract-retract mechanism of a ratchet and plunger type, as shown in FIG. 6. In one example the connection comprises both a locking means and a protract-retract mechanism.

The tool may be made of any suitable material. The material may be transparent, partially opaque, or completely opaque. The tool may be made of one material only, or it may be made of two or more different materials, for example rigid materials such as rigid plastics or metals, and elastic materials. For example the injection guide may comprise rigid transparent plastics and the stabilizer may comprise non-transparent material, such as metal, but has a flange comprising elastic material, such as rubber.

In one embodiment the injection guide is made of transparent material, making the needle and the point of injection visible to the user. The injection guide may be made of the same material as the stabilizer. In one example all the parts or portions of the tool are made of the same material, i.e. the tool consists of one type of material only, excluding any possible markings such as ones made with ink or paint or the like. The material may be thermoplastic polymer, in general plastic, which is usually rigid, i.e. non-flexible or non-elastic. Medical grades may be used. Examples of suitable thermoplastic polymers include polycarbonates, polyamides, such as transparent thermoplastic polyamides based on aliphatic, cycloaliphatic and aromatic blocks, or amorphous polyamides, polyoxymethylene copolymers (POM), such as copolymeric polyacetal resins, and the like. Examples of commercially available useful materials include Grilamid (polyamides), Kocetal, and Kepital (polyoxymethylene copolymers). In one example the stabilizer and the injection guide are made of the same material, which may be rigid material, but the tool further comprises elastic parts or portions as described herein, for example an elastic part in the protruding portion of the injection guide, in the aperture in the stabilizer, in the flange or in the one or more stoppers inside the injection guide.

In one example the injection guide is a hollow cylinder that is adapted to receive the dispensing end of an injection needle and to hold the needle in a desired position. The inner dimensions of the cylinder are adapted to the outer dimensions of the needle, hub, connector or syringe. The injection guide may also be of any other suitable shape.

The injection guide may comprise returning means for returning the needle backwards within the injection guide, without retracting the injection guide itself. The returning means may be a flexible element, for example a spring, a flexible or elastic protrusion, or compressible, bending, twisting, mechanical and/or otherwise moving material.

The purpose of the returning means is to return the needle backwards inside the injection path, to create a tunnel-like pathway to enable a better flow of substance into and out of the injection point.

The returning means may be located in the base or in the lower part of the cylinder of the injection guide. Alternatively, the returning means may be a removable ring attached directly onto or around the needle. The returning means may also be located at the connection with the locking means between the injection guide and the base.

Figure 6A:
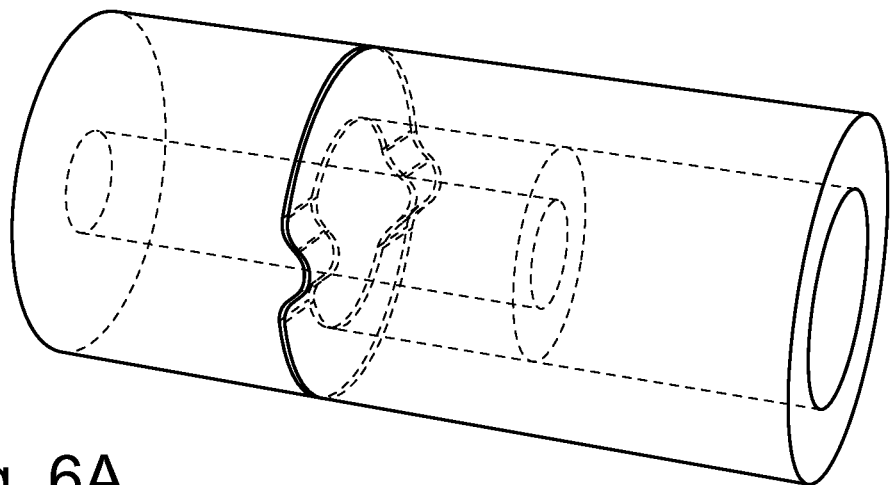
FIG. 6 shows a protract-retract mechanism based on a ratchet and plunger mechanism, which mechanism can be used in an embodiment.
Figure 6B:
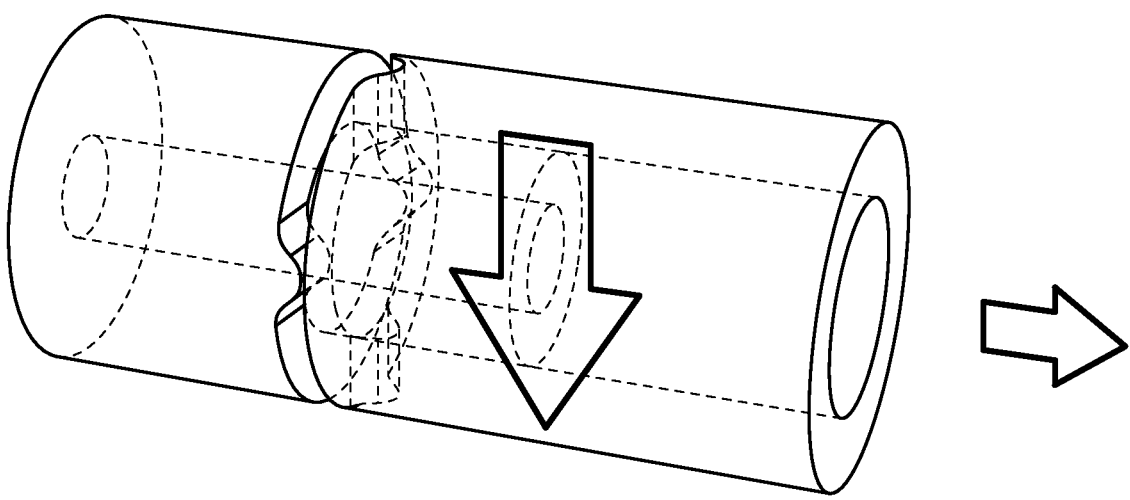

The returning means may be implemented for example as a protract-retract mechanism based on a ratchet and plunger mechanism as described in the patent publication U.S. Pat. No. 3,288,115, which uses such a mechanism in connection with a ball point pen. In connection with the embodiments, such a protract-retract mechanism could first protract the needle and thereafter retract it for a small distance to enable better drug flow. FIG. 6 shows such a mechanism: in FIG. 6A the mechanism is in a protracted state, and in FIG. 6B the mechanism is in a retracted state. The therapeutic effect of the injected substance, such as a fluid drug formulation, is improved when using such a protract-retract mechanism, as drug flow and diffusion are improved.

The whole ocular therapeutics tool or any part of it may be made of a controllably flexible material.

A handle may be connected to an upper part of the body. The handle enables the user to hold the tool firmly, for example by using his thumb and two other fingers, like a hypo. The handle may have any suitable shape such as circular, oval, or wing-like. The tool may be constructed without any handle as well. Exemplary handles 27 and 57 are shown for example in FIG. 2A, FIG. 5D, FIG. 12A, FIG. 13B. When using non-circular handle, such as a wing-like handle, the user knows immediately where the injection site is located. The wing-like handle refers to a handle having two wings, i.e. flat extensions, extending from the first end of the body to opposite directions, as shown for example in the FIGS. 2A, 5D, 12A and 13B.

In an embodiment shown in FIG. 5D and FIG. 12A, the handle 57 and the hollow body 54 have a roughened texture on a part of their outer surface to enable a firm hold. The surface may be for example corrugated or grooved, either partly or completely.

Upon using the ocular therapeutics tool, the user may block the upper opening 58 of the body 54 by his thumb so that the patient cannot see the delivery of an injection.

Preferably, the shape of the tool is symmetrical in the sense that it can be applied for the left eye or the right eye as well. The tool may be disposable or, alternatively, it may be used several times.

The tool may be adapted to be used together with a surgical drape or a drape like product, such as a lid speculum (LiDrape®), which can be removable or integral to the tool. Such drapes are well known in the art.

In an embodiment, the body comprises an opening, for example at the side of the body, that is adapted for making a puncture in the cornea paracentesis by means of a knife or a needle in order to release any intraocular pressure. Such an opening may also enable the user to visually better observe the eye during positioning of the tool. Exemplary openings 15, 35, 55 are shown in FIG. 1, FIG. 3, FIG. 5D, FIG. 12 A and FIG. 12B.

The tool is preferably used for making injections to the suprachoroidal and intrascleral space of the eye and to the cornea. The tool may be used for making injections to the subretinal space of the eye.

The tool may be used to remove substances, such as a fluid, tissue, or molecule samples, from the eye.

The tool may be used in connection with obtaining a sample from the fluid in the SCS or other structures of the eye. The fluid may be withdrawn through a needle while the needle remains within the tool in an inserted position in the ocular tissue. Alternatively, the fluid may flow out through an aperture left in the ocular tissue after the needle has been withdrawn from the tissue.

Tissue may be removed by a coring method related to conventional biopsies. Molecules may be removed by binding molecules to the needle. The binding may be a selective chemical binding.

The tool according to the embodiments can be used in connection of sensors to detect analytes, electrical activity, and optical or other signals from the eye. Such sensors may include sensors of pressure, temperature, chemicals, and/or electromagnetic fields (e.g. light). The sensors may also be biosensors located on the surface of a needle, inside a needle, or inside a device in communication with the body tissue via a needle. The biosensors can be potentiometric, amperometric, optical, or physiochemical. Also optical fibers may be inserted into eye by using the tool.

In one embodiment, a hollow needle is filled with a substance, such as a fluid or gel, which has a sensing functionality associated with it. In an application for sensing based on binding to a substrate or reaction mediated by an enzyme, the substrate or enzyme can be immobilized in the needle interior. In another embodiment, a wave guide or an optical fiber is incorporated into the needle to direct light to a specific location, or for detection, for example, using means such as a pH dye for colour evaluation. Similarly, heat, cold, electricity, light or other energy forms may be precisely transmitted to directly stimulate, damage, or heal a specific tissue or for diagnostic purposes. In one embodiment a biodegradable needle, which may remain in the eye, is used. Biodegradable needles may comprise biodegradable polymers, such as polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, or copolymers and blends thereof.

In general, the tool can be used for various purposes, such as for taking samples and biopsies, for measuring electrical conductivity via needle electrodes, for stimulation, for imaging purposes, for laser treatments, for illumination, for measuring temperatures, or for measuring the pH within the eye.

The embodiments are widely applicable to all kinds of treatments or measurements of the eye that require positioning of a needle-like instrument or a corresponding medical device within a specified depth within the internal structures of the eye. Besides ophthalmology, the embodiments may also be used in other fields of medicine, e.g. dentistry, aesthesis, transdermal substance delivery and extraction, injections of insulin and vaccines, targeted medication delivery with pinpoint accuracy, local anaesthesia, biopsies, such as aspiration biopsies, especially fine needle aspiration biopsies (FNAB) for uveal melanoma, and sample taking, in vivo and ex vivo drug testing on humans and animals.

The needle to be used in connection with the tool may be any needle that is adapted for responding to the stopper or to the adjustment means so that an effective injection depth (i.e. an actual penetration depth into the eye tissue) becomes defined. The needle may be for example a hypodermic needle, an insulin needle, a drug-coated solid needle, an epidural needle, a biodegradable needle, a cannula, a probe, a fibre, a cable, or any needle or other punctuation member that is used for example in connection with particular imaging, operation or measurement devices. A drug-coated needle may be used for example when the injection is targeted into a very thin layer in the eye, for example a layer in the cornea, which cannot receive a remarkable volume of injectable fluid. Examples of such treatments include reduction or inhibition of neovascularization, and corneal collagen crosslinking for treating corneal ectasia such as keratoconus, wherein riboflavin is administered into cornea with pinpoint accuracy. The term "injecting" or "injection" as used herein may refer to either administering the injectable substance as a fluid, solution, suspension, emulsion or the like from a container, for example by using a syringe, or to administering the substance as a coating on a needle.

In one embodiment, the tool is adapted for a regular injection needle. The length of a regular injection needle is typically more than 10 mm, for example about 13 mm (½"). Preferably, the tool is adapted for a hypodermic needle having a size of 20-33 G or smaller. A "hypodermic needle" as used herein refers to an injection needle which is not a microneedle, and has a gauge in the range of 7-40 G, such as in the range of 20-40 G, for example 33 G, 30 G, 29 G, 27 G or 21 G. The length of a hypodermic needle may be in the range of 10-40 mm, or longer. A microneedle is an injection needle having a length of 2.5 mm or 1.0 mm or less.

One embodiment provides a kit comprising the ocular therapeutics tool described herein, or the injection guide described herein, or the stabilizer described herein, and optionally at least one needle and/or syringe and/or medicament vial or a vial comprising any other injectable substance. The kit may also contain a drape or any other materials or instrument(s). The kit, or the content thereof, may be sterilized and it may be hermetically sealed and comprising a package, such as an inner package, covered with a removable cover, such as a plastic membrane which is arranged to be removed before use, for example by tearing. The package may contain sterile and/or protective gas or vacuum.

In one embodiment the injection guide is positioned onto a support pickable with a needle installed to a syringe. This means that the injection guide may be picked by pushing a needle installed to a syringe into the injection guide, i.e. it is not necessary to use hands for picking the injection guide from the package included in the kit. The support may be formed inside the kit, which is usually provided in a box, for example a cardboard box. The support may be made of plastics, which is designed to hold one or more of the components included in the kit. The support may be called as an inner tray. An inner tray in general may be formed for example by pressing or it may be vacuum-formed and/or vacuum thermoformed. The support material may be any suitable material, such as plastic, for example HIPS, ABS, PET, polystyrene etc. or elastic material, or it may comprise elastic and rigid materials. The injection guide may be positioned in such way that when the user has installed a needle into syringe, and optionally filled the syringe with medicament, the syringe may be pushed in such way that the needle enters the injection guide until the stopper is in contact with the hub of the needle. After this the injection guide is installed, i.e. attached or locked to the needle and/or syringe, and the needle has a first effective length. When the syringe is lifted the injection guide follows i.e. the injection guide is picked. If the injection guide has an adjusting means, the effective length of the needle may be further adjusted to obtain a second effective length of the needle, which may be the final effective length which is used for making the injection.

Figure 14A:
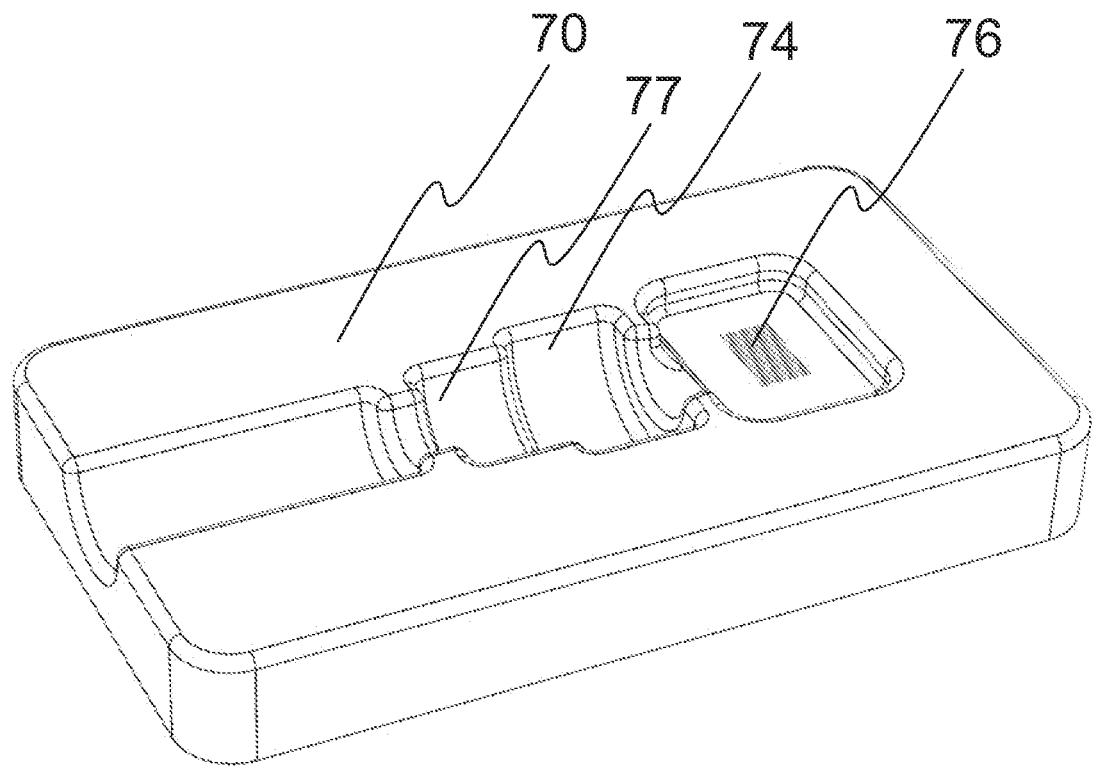
FIGS. 14A-C show a measuring scale for determining the effective length of the needle.

The effective length of the needle may be checked by using a microscope, magnifying glass or any other magnifying means for monitoring the length of the needle protruding from the injection guide. A measuring scale may be used for determining the actual effective length. In one embodiment a kit comprises a measuring scale for determining the effective length of the needle. The measuring scale may have distance markings representing a range of effective lengths of the needle. In one embodiment as shown in FIG. 14a the kit is provided with a measuring scale 76 adapted to receive the injection guide, for example on a support 70, which may also be called as an inner tray as explained above, made of plastics or other material, the support containing the scale 76 and a slot 74 for receiving the injection guide 12, for example connected to a syringe 36. One embodiment therefore comprises a support adapted to receive the injection guide 52, the support 70 containing the measuring scale 76 and a slot 74 for receiving the injection guide.

Figure 14B:
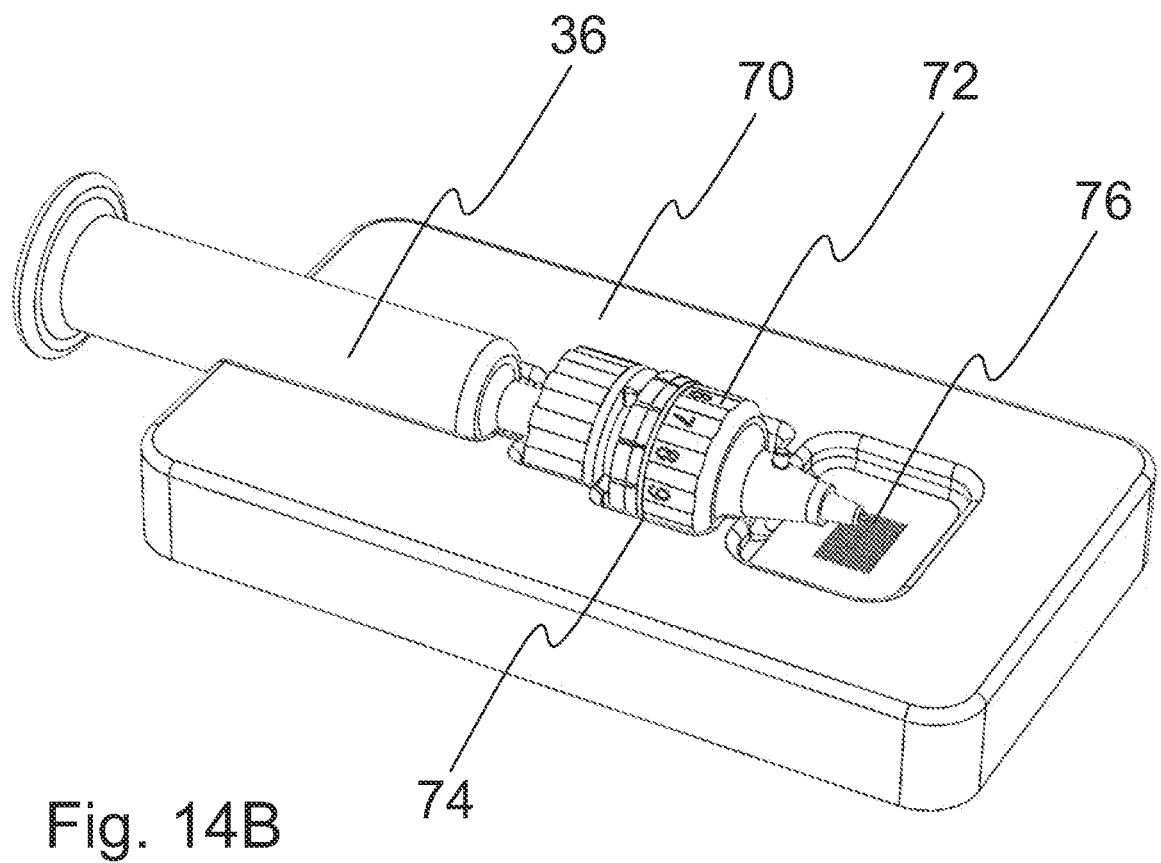
Figure 14C:
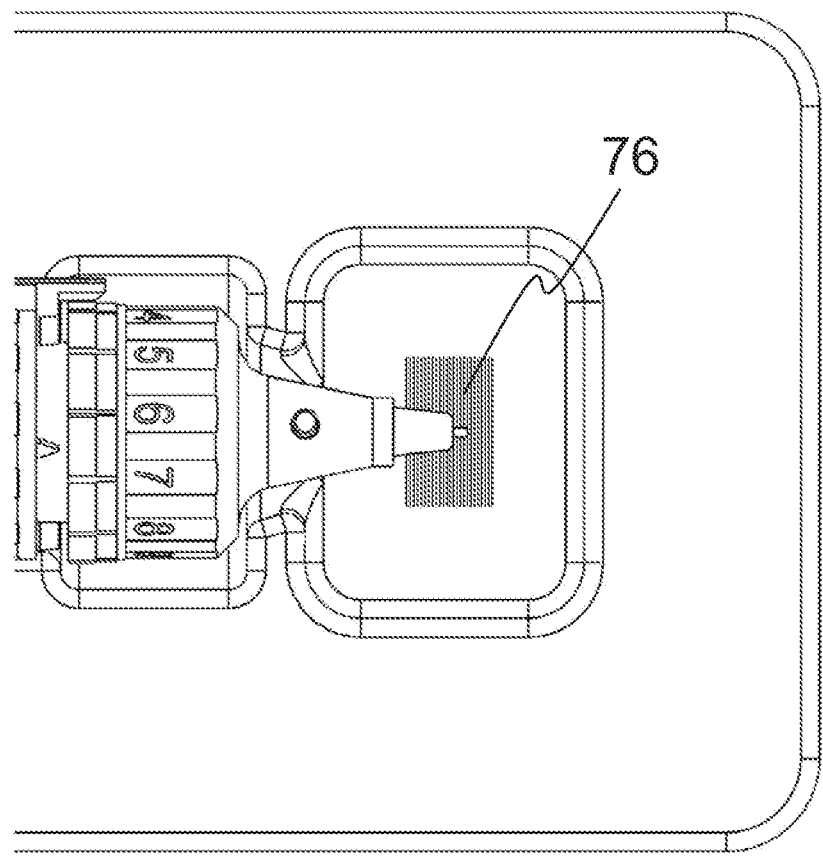

The slot 74 may be arranged to lock or stabilize the injection guide 72 and optionally also the syringe 36 when force is applied by pressing the injection guide 72 into the slot 74. A material providing high friction such as rubber or the like may be used in the support, for example as a coating on the support or on a portion of the support or the slot, to facilitate stabilizing the injection guide. In such case the injection guide, preferably with an inserted needle, is placed into a designed slot in a measuring scale support, or the needle is inserted to an injection guide already in the slot, wherein the injection guide is positioned in such way that the effective length of the needle can be defined by comparing to a scale or a rule, which may be behind or at the side of the needle, as shown in FIG. 14b. The kit may also be provided with the injection guide already placed onto said support, for example with the needle installed into the injection guide. The scale or the rule may contain parallel lines or other markings at predetermined intervals, such as at 50 µm or 100 µm intervals. In one example the scale contains lines at 100 µm intervals. The effective length of the needle may be determined by comparing the protruding length of the needle to the lines in the scale as shown in FIG. 14C, for example by using a magnifying means, such as a magnifying glass or a microscope. The effective length of the needle may be then adjusted and monitored. In one embodiment the injection guide is adjustable while located on the support, for example the second part of the injection guide may be turned to change the effective length of the needle, and the change in the protruding length of the needle can be seen and measured immediately. In such case the support may be designed to allow the adjustment of the second part of the injection guide only while the movement of the first part of the injection guide is inhibited for example by using a material with high friction on the part 77 of the slot which is in contact with the first part of the injection guide, for example a rubber coating or a like. Alternatively the portion 77 is designed to tightly fit to the first part of the injection guide to prevent the first part from moving when the second part is adjusted. In one example the kit is provided with a magnifying glass, which may be for example made of plastics or glass or other material, preferably inexpensive material. The magnifying glass may be adapted to be positioned above the scale, or it may be already positioned onto the support above the scale and above the needle. The support may be designed to hold the magnifying glass at a suitable position and distance from the needle and/or the measuring scale.

When using a measuring scale or a similar aid which enables measuring or otherwise determining the effective length of the needle after the needle has been inserted into an injection guide, especially when an adjustable injection guide is used, practically any needle may be used. The length of the needle does not have to be in a predetermined tolerance or variance range, so no preselected needles are necessarily required.

In one embodiment a needle length gauge tool is provided, which may be used for determining the effective length of the needle. In one embodiment the needle length gauge tool is a piece containing plurality of portions comprising an aperture for a needle and a specific thickness around the aperture, each specific thickness being different and representing different possible effective lengths of a needle. The different effective lengths are indicated in the piece, for example by numerical values printed beside every aperture. A needle installed into an injection guide is inserted into a single aperture and the protrusion of the needle tip from the gauge tool is checked. If the tip of the needle is not visible, the needle is inserted into another aperture at another portion having a different thickness, preferably thinner than in the previous portion, and the protrusion of the needle tip from the gauge tool is checked again. When the tip of the needle is visible for the first time, the effective length of the needle can be read from the gauge tool and it corresponds to the length indicated in that portion. The needle length gauge tool may be for example a flat piece of plastic having protruding flat portions at the edges of the piece. A needle length gauge tool may provide a series of thicknesses for predetermined effective lengths of the needle, for example with an interval on 50 or 100 µm, for example the predetermined effective lengths of 600, 650, 700, 750, 800, 850, 900, 950 and 1000 µm; or 600, 700, 800, 900, 1000 and 1100 µm, or any other lengths disclosed herein. Also other type of gauge tools may be used, such as feeler gauge or Vernier caliper type of gauge tools, or any other suitable gauge means for determining the effective length of the needle, especially by using magnifying means and comparing the length of the needle to the gauge means.

Alternatively, a series, meaning at least two, of injection guides providing different effective lengths may be provided in the kit. In one embodiment the kit comprises at least two injection guides, i.e. a plurality of injection guides, each providing different predetermined effective lengths of the needle. Such injection guides do not need further adjustment means, so in one embodiment the injection guide does not contain such an adjustment means as described above. A series of injection guides having predetermined effective lengths of the needle may be provided for example with an interval on 50 or 100 µm, for example injection guides providing the predetermined effective lengths of 600, 650, 700, 750, 800, 850, 900, 950 and 1000 µm; or 600, 700, 800, 900, 1000 and 1100 µm. Examples of such ranges include 500-1000 µm, 600-1000 µm, 600-900 µm, 700-1000 µm, 700-900 µm, and even ranges up to 1200 µm, for example 600-1200 µm, 700-1200 µm, 800-1200 µm, 600-1100 µm, 700-1100 µm or 800-1100 µm, all with either 50 µm or 100 µm intervals. Similar ranges may be provided by the adjustable injection guides. In one embodiment the series of injection guides are positioned onto a support pickable with a needle installed to a syringe. Said support may also be called as an inner tray as explained herein.

In one embodiment the kit comprises a vial containing medicament or other substance for injecting into the eye, for example into the suprachoroidal space of the eye. In one example the vial is a prefilled syringe. The medicament or the other injectable substance may be dried, or it may be in a solution, in an emulsion or in a suspension, aqueous or non-aqueous. A dried substance must be brought into a form of a solution, an emulsion or a suspension before injecting by adding solvent, such as distilled water. The "injectable substance" as used herein refers to any substance to be injected into the eye as described herein, including substances in solutions, emulsions, suspensions and the like, and dried substances.

As there may be a variance in the dimensions of commercially available hypodermic needles, which may affect the accuracy of the injection, it may be advantageous to provide preselected needles wherein the needle length is precisely known, especially the length of the needle from a hub to the tip of the needle is known. The length of the needle is in a predetermined tolerance or variance range, for example having a variance in the range of 10-100 µm, or even 10-50 µm, or 10-30 µm, or 10-20 µm, or 20-50 µm, or more particularly about 50, about 40, about 30, about 20, or about 10 µm, even about 5 µm. With a preselected needle the effective first length of the needle can be standardized and the error in the length can be minimized. The needle having a predetermined needle length is adapted to provide a predetermined effective length of the needle when used with the injection guide provided in the kit.

In one embodiment the kit comprises at least one needle, such as a hypodermic needle or any other suitable punctuation member, having a predetermined needle length, which may be measured from a hub of the needle, in general to the tip of the needle, within tolerance range of 10-100 µm, such as 10-50 µm, or 10-20 µm, or other range mentioned above. The predetermined needle length may also be measured from a connector to the tip of the needle, or from the glued portion in the juncture of the needle shaft and the hub to the tip of the needle.

One embodiment provides a method for injecting substance to an eye, the method comprising
  providing the ocular tool described herein,
  providing a substance for injection,
  inserting a punctuation member connected to a container containing the substance into the injection guide,
  positioning the stabilizer to the eye,
  inserting the injection guide to the stabilizer, and
  injecting the substance to the eye.

One embodiment provides a method for injecting substance to an eye, the method comprising
  providing the ocular tool described herein,
  providing a substance for injection,
  inserting a syringe containing said substance with a needle into the injection guide,
  positioning the stabilizer to the eye,
  inserting the injection guide to the stabilizer, and
  injecting the substance to the eye.

The injection may be carried out also with a punctuation member, for example a needle which may be solid or hollow, which is covered with the injectable substance, i.e. there is no separate container containing the injectable substance. The punctuation member may be dipped into the injectable substance before the injection, or the punctuation member may be provided with the injectable substance on the tip of the member, for example as a layer of the substance applied on the punctuation member. This may be useful for example in cases where a large volume of substance cannot be injected to the target, for example when the target tissue does not have a potential space.

In one embodiment the injection is directed into suprachoroidal space of the eye. In one embodiment the needle is a hypodermic needle. The substance for injection may also be called as injectable substance.

One embodiment provides a method for injecting substance to an eye with a normal size needle, such as a hypodermic needle, or with a non-microneedle, for example into suprachoroidal space of the eye or into the cornea, with any of the methods described herein.

In one embodiment the method comprises, after inserting the syringe containing said substance with a needle into the injection guide, adjusting the injection guide to obtain a desired effective length of a needle, as described herein. In one embodiment this is carried out before inserting the injection guide to the stabilizer.

After the injection the injection guide may be disconnected and removed from the stabilizer. In a case wherein the injection is not successful, for example if the injection depth was incorrect, the injection guide may be disconnected and removed from the stabilizer and the stabilizer is left in the eye. A new injection depth, for example with a new injection guide and/or needle, is defined and the injection guide is inserted to the stabilizer already in the eye. It is also possible to slightly change the injection site at this phase by moving the stabilizer in the eye, for example by rotating. In case wherein there are several injection points the stabilizer may be left in the eye after the first injection in similar way and a subsequent injection is carried out a new injection point.

In one embodiment the method comprises providing a series, meaning at least two, of injection guides each providing a different effective length, for example in a kit, as described herein, and choosing an injection guide providing a desired effective length of a needle. The desired effective length is a length which provides the desired injection depth for the patient to be treated, as described herein.

One embodiment provides a method for injecting substance to an eye, the method comprising
  providing the injection guide described herein,
  providing a substance for injection,
  inserting a punctuation member connected to a container containing the substance into the injection guide,
  inserting the injection guide into an eye, and
  injecting the substance to the eye.

One embodiment provides a method for injecting substance to an eye, the method comprising
  providing the injection guide described herein,
  providing a substance for injection,
  inserting a syringe containing said substance with a needle into the injection guide,
  inserting the injection guide into an eye, and
  injecting the substance to the eye.

In the following the use of the tool is explained in practice according to exemplary embodiments.

In an embodiment, wherein adjustment means based on screw threads and a removable injection guide are used, the method comprises
positioning a base of the tool under the eyelids,
inserting a needle into an injection guide,
adjusting the needle length to a desired injection depth,
inserting the injection guide to a stabilizer of the tool,
performing an injection of a substance,
retracting the needle from the injection guide,
removing the stabilizer from the eye.

The substance that can be used in connection with the present ocular therapeutics tool may be chosen among all drugs, formulations, compositions and substances that are capable of providing a therapeutic effect when administered into the eye. For example, the tool may be used for implanting nanomaterials to strengthen a weak cornea. The substance is to be administered in an amount sufficient to provide a therapeutic effect.

Example

Figure 9:
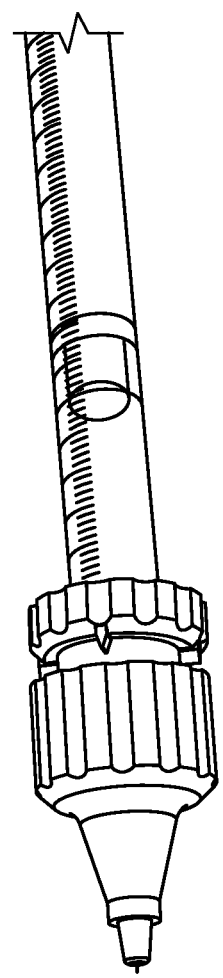
FIG. 9 shows the tool that was used in the Example presented below, for obtaining the results shown in FIGS. 7 and 8.
Figure 9:
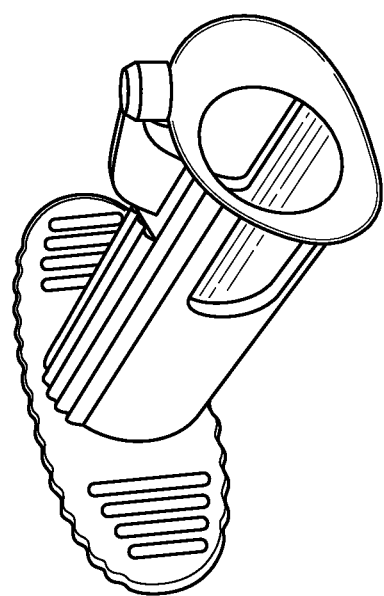

The tool according to an embodiment was tested by making SCS injections into porcine eyes. The structure of the tool used is shown in FIG. 9.

The tool was used together with hollow needles (a 33 G injection needle with a total length of 13 mm, VitaNeedle) to inject 1% methylene blue (Sigma-Aldrich; M9140-25g) and 1 µm carboxylate-modified Fluorospheres (Molecular Probes; F8821) into the suprachoroidal space. The injected eyes were fixed with 4% paraformaldehyde overnight at +4° C. and processed either for paraffin embedding or cryosectioning. After that the eyes were microsectioned and the sections were counterstained and analyzed using light (for eyes injected with methylene blue) or confocal (FluoSpheres) microscopes.

1% methylene blue solution prepared in distilled water, and 1 µm red (580/605) carboxylate-modified FluoSpheres were used. The dyes were taken up by 1 ml syringe and the injections were performed under the stereomicroscope using the following parameters:

1) Effective needle lengths were 800-900 µm. The total length (13 mm) of the needle was limited by means of adjustment means based on screw threads.
2) The needles were inserted perpendicular to tissue approximately 7 mm posterior from the limbus of porcine eyes.
3) 1 ml of the dyes were injected in a controlled fashion into the suprachoroidal space.

The tissue was sectioned and the sections were counterstained. The pictures were taken with Leica microscope or LSM700 confocal microscope (Zeiss GmbH). The distribution of the dyes was successfully verified from the ocular sections at the suprachoroidal space.

Figure 7:
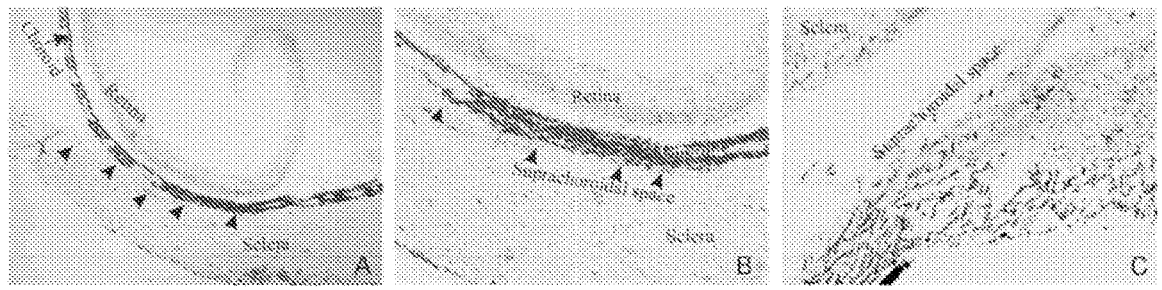
FIG. 7 shows the results from methylene blue injections into porcine eyes. Pictures taken with low (FIG. 7A) and high (FIGS. 7B and 7C) magnifications show the distribution of methylene blue in the suprachoroidal space (black arrows).

Methylene blue was found in the suprachoroidal space, see FIG. 7.

Figure 8:
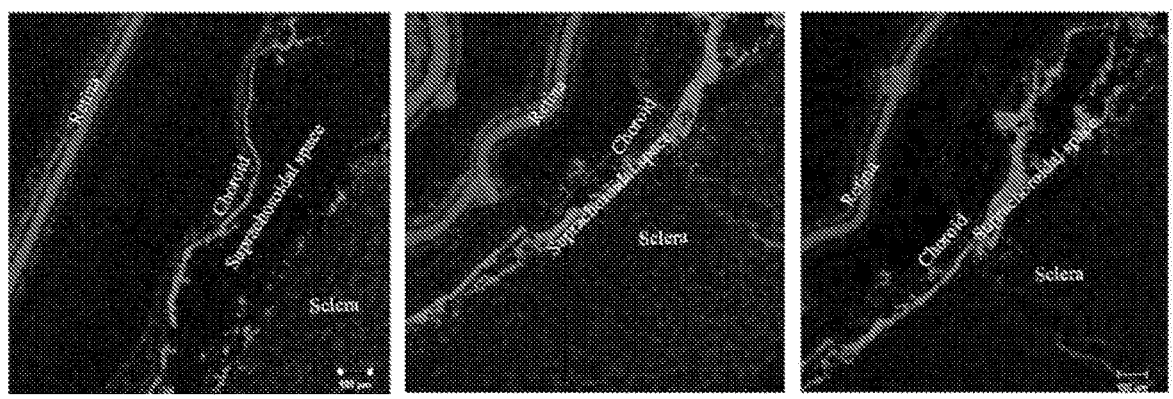
FIG. 8 shows the results from injections of 1 μm red carboxylate-modified Fluorospheres (Molecular Probes; F8821) into porcine eyes. All pictures were taken with a confocal microscope to visualize fluorescent (in red) Fluo-Spheres. Tissue counterstain is shown in blue (DAPI staining).

Similarly as with methylene blue, the confocal analysis from porcine ocular sections revealed that 1 µm FluoSpheres (in red) were localized in the suprachoroidal space, see FIG. 8.

The results show that the tool is well suitable for precise delivery of injected material into suprachoroidal space.

The invention claimed is:

1. An ocular therapeutics tool, comprising:
   a stabilizer comprising a hollow body and a base connected to the hollow body, the hollow body extending from the base, an inside of the hollow body being open in such way that the iris of an eye can be seen through the hollow body when inserting the stabilizer into the eye, and the base comprising a flange adapted to fit an eye surface, and
   an injection guide removably connectable to the stabilizer and adapted to receive a needle attached to a syringe,
   wherein the injection guide comprises at least one stopper adapted to define an injection depth of the needle inserted into the injection guide,
   wherein the injection guide comprises a protruding portion adapted to fit to an aperture in the stabilizer,
   wherein the protruding portion of the injection guide is adapted to contact the eye surface through the aperture in the stabilizer during the use,
   wherein the flange comprises an annular support surface adapted to fit the eye surface, and
   wherein the aperture is formed on the annular support surface and adapted to receive the injection guide.

2. The ocular therapeutics tool of claim 1, wherein a connection between the protruding portion of the injection guide and the aperture in the stabilizer comprises locking means for stabilizing the needle when inserted.

3. The ocular therapeutics tool of claim 1, wherein the injection guide is removably connectable to the stabilizer via a support arm in the stabilizer.

4. The ocular therapeutics tool of claim 1, wherein the needle comprises an injection needle.

5. The ocular therapeutics tool of claim 1, wherein the base comprises, at a side in contact with the eye surface, one or more openings around the aperture adapted to receive the injection guide.

6. The ocular therapeutics tool of claim 1, wherein the base comprises, at a side in contact with the eye surface, one or more protruding portions around the aperture adapted to receive the injection guide.

7. The ocular therapeutics tool of claim 1, wherein the injection guide comprises adjustment means for adjusting a final effective length of the needle, and wherein the at least one stopper is adapted to contact a hub of the needle to stop the needle.

8. The ocular therapeutics tool of claim 1, wherein the injection depth is defined by providing an effective length of the needle protruding from the injection guide of less than 1200 µm such as that the injection depth of the needle is within the suprachoroidal space of the eye.

9. The ocular therapeutics tool of claim 1, wherein the at least one stopper is adapted to contact a connector of the needle to stop the needle.

10. The ocular therapeutics tool of claim 1, wherein the injection guide comprises a bore for receiving the needle, and the at least one stopper comprises at least one elongated projection on a surface of the bore parallel to the axis of the bore.

11. The ocular therapeutics tool of claim 1, wherein the injection guide comprises a bore for receiving the needle, and the at least one stopper comprises at least one edge on a surface of the bore.

12. The ocular therapeutics tool of claim 1, wherein the injection guide comprises a bore for receiving the needle, and an edge surrounding the bore is adapted to act as the at least one stopper.

13. The ocular therapeutics tool of claim 1, wherein the base comprises, at a side in contact with the eye surface, one or more cavities or pits having a depth in the range of 0.2-1.0 mm.

14. The ocular therapeutics tool of claim 1, wherein there is a clearance in the range of 10-200 µm between the protruding portion and the aperture in the stabilizer during use.

15. The ocular therapeutics tool of claim 1, wherein the protruding portion fits the aperture in the stabilizer with such an accuracy that the injection guide does not move substantially during use.

16. The ocular therapeutics tool of claim 2, wherein the locking means comprise a bayonet type of coupling.

17. The ocular therapeutics tool of claim 5, wherein the one or more openings extend through the base, having a depth in the range of 0.2-1.0 mm.

18. The ocular therapeutics tool of claim 5, wherein the one or more openings are round apertures smaller than the aperture in the stabilizer, or they are elongated relative to the aperture in the stabilizer.

19. The ocular therapeutics tool of claim 7, wherein the adjustment means comprises a stepwise adjustment.

20. The ocular therapeutics tool of claim 8, wherein the effective length of the needle is in the range of 500-1200 µm.

21. The ocular therapeutics tool of claim 8, wherein the effective length of the needle is in the range of 50-700 µm.

22. The ocular therapeutics tool of claim 10, wherein the at least one elongated projection is beveled in the longitudinal direction of the bore towards the first end of the injection guide, which end is adapted to receive the needle.

23. The ocular therapeutics tool of claim 20, wherein the effective length of the needle is in the range of 600-1000 µm.

24. The ocular therapeutics tool of claim 21, wherein the effective length of the needle is in the range of 400-700 µm.

25. A kit comprising the ocular therapeutics tool of claim 1, and at least one needle and/or syringe and/or vial containing injectable substance and/or drape.

26. The kit of claim 25, further comprising at least one injection guide positioned onto a support pickable with a needle installed to a syringe.

27. The kit of claim 25, further comprising at least two injection guides each providing different predetermined effective lengths of the needle.

28. The kit of claim 25, further comprising a vial containing a medicament or other substance for injecting into the eye, for example into the suprachoroidal space of the eye.

29. The kit of claim 25, further comprising at least one needle, such as a hypodermic needle, having a predetermined needle length, for example measured from a hub of the needle to the tip of the needle within tolerance in the range of 10-100 µm, such as 10-50 µm, or 10-20 µm.

30. The kit of claim 25, further comprising a measuring scale for determining the effective length of the needle.

31. The kit of claim 30, further comprising a support adapted to receive the injection guide, the support containing the measuring scale and a slot for receiving the injection guide.

* * * * *